United States Patent [19]
Saito et al.

[11] Patent Number: 5,568,530
[45] Date of Patent: Oct. 22, 1996

[54] X-RAY COMPUTED TOMOGRAPHY APPARATUS

[75] Inventors: Yasuo Saito, Tochigi-ken; Tsuyoshi Hatano, Otawara, both of Japan

[73] Assignee: Kabushiki Kaisha Toshiba, Kawasaki, Japan

[21] Appl. No.: 417,785

[22] Filed: Apr. 6, 1995

[30] Foreign Application Priority Data

Apr. 8, 1994 [JP] Japan .................................. 6-070561

[51] Int. Cl.⁶ ........................................................ A61B 6/03
[52] U.S. Cl. ......................... 378/4; 378/901; 364/413.16
[58] Field of Search .................. 378/4, 901; 364/413.14, 364/413.15, 413.16

[56] References Cited

U.S. PATENT DOCUMENTS

| | | | |
|---|---|---|---|
| 4,260,894 | 4/1981 | Neumann | 378/16 |
| 5,142,286 | 8/1992 | Ribner et al. | 341/143 |

*Primary Examiner*—David P. Porta
*Assistant Examiner*—David Vernon Bruce
*Attorney, Agent, or Firm*—Oblon, Spivak, McClelland, Maier & Neustadt, P.C.

[57] ABSTRACT

An X-ray computed tomography apparatus in which detection signals based on X-rays transmitted through an object to be examined are repeatedly integrated at predetermined intervals. The integral signal is sampled a plurality of times in an initial period of the interval, and the sampled signals are averaged. The integral signal is also sampled a plurality of times in a final period of the interval, and the sampled signals are averaged. Projection data are created by subtracting the initial average value from the final average value. Circuit noise can be reduced according to the increase in number of times of sampling with a detioration in X-rays available for processing since the integration time is substantially shortened. Circuit noise becomes conspicuous when the dose of transmitted X-rays is relatively small, and becomes latent when the dose of X-rays is relatively large. The number of sampling times is controlled by oversampling on the basis of scan conditions which allow estimation of the dose of transmitted X-rays in such a manner. When the dose of transmitted X-rays is relatively small, the circuit noise reducing effect can be improved at a cost of a reduction in the amount of X-rays available for processing. When the dose of transmitted X-rays is relatively large, the amount of X-rays available for processing can be improved.

28 Claims, 16 Drawing Sheets

$D1 < D2 < D3 < D4 < D5 < D6$
$M1 < M2 < M3 < M4 < M5$

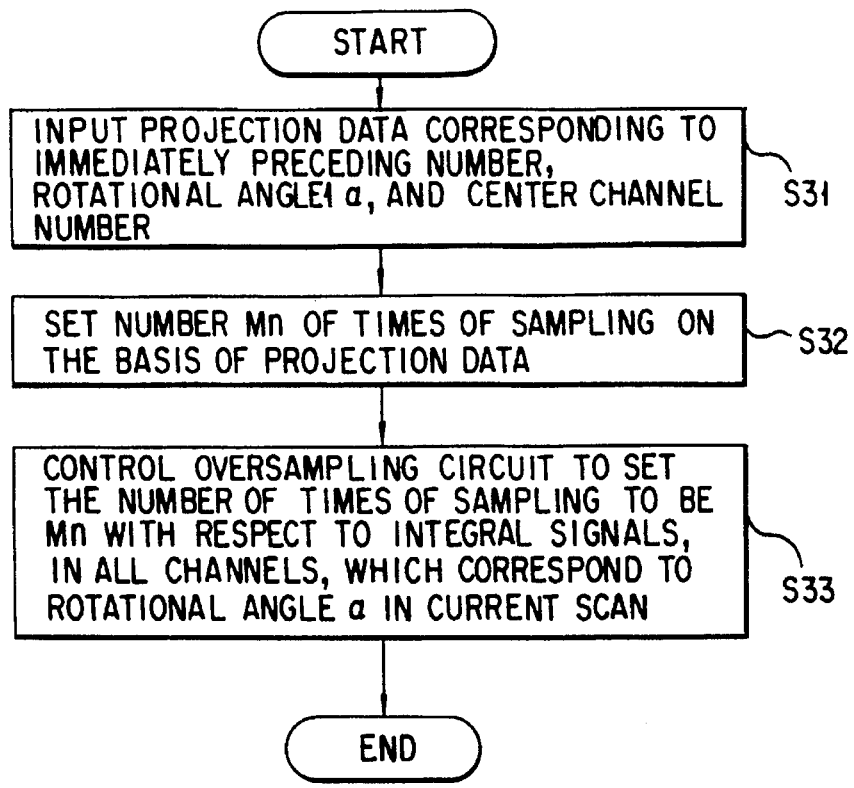
F I G. 11A
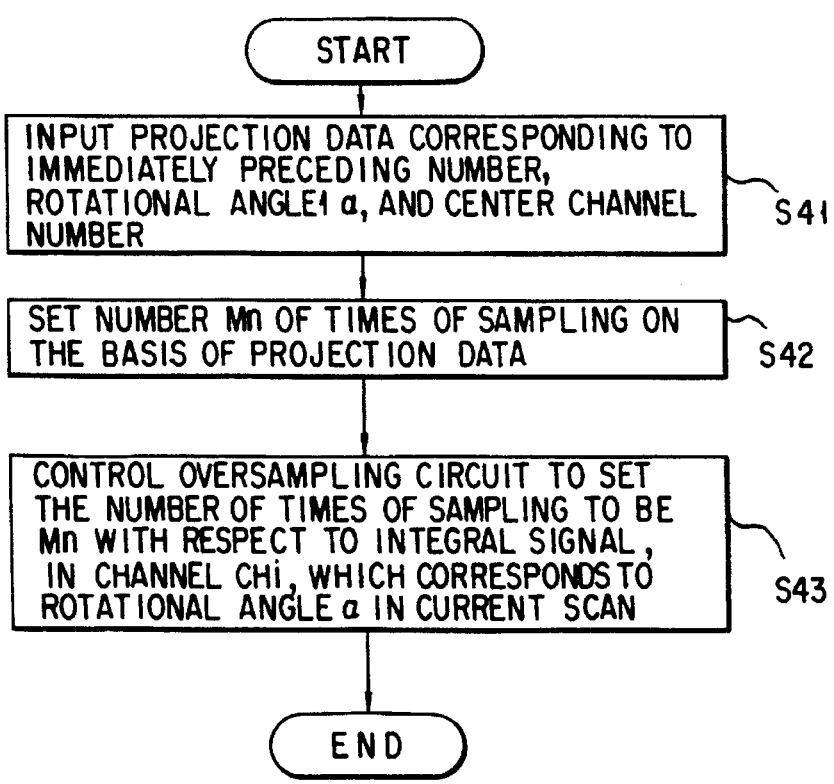
F I G. 11B

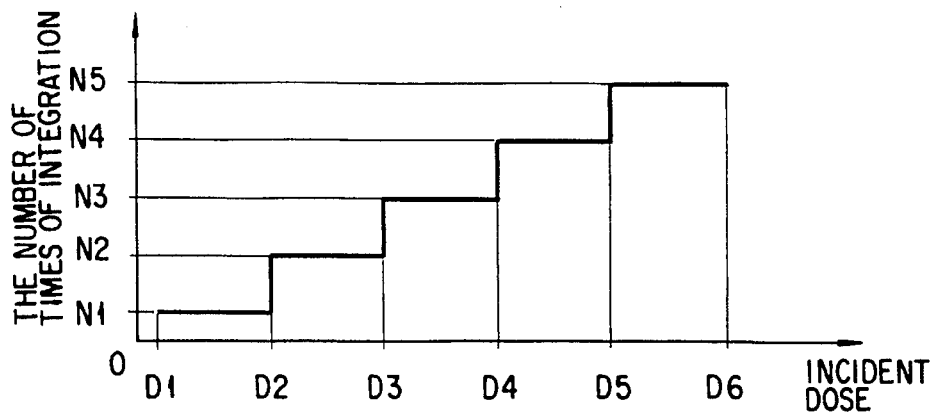
FIG. 13   D1<D2<D3<D4<D5<D6
N1<N2<N3<N4<N5
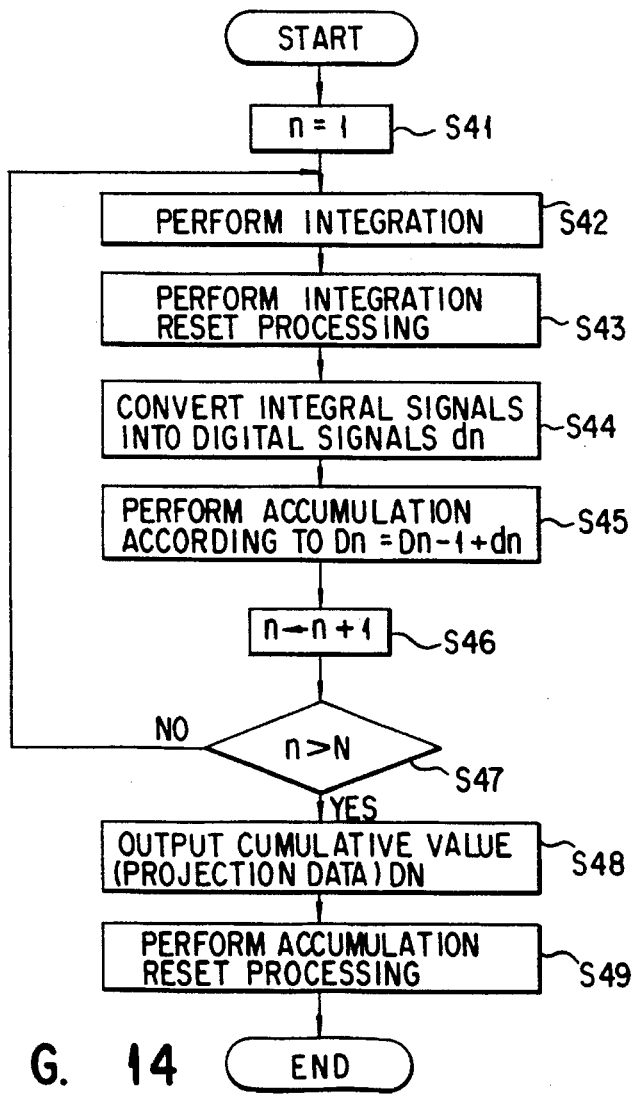
FIG. 14

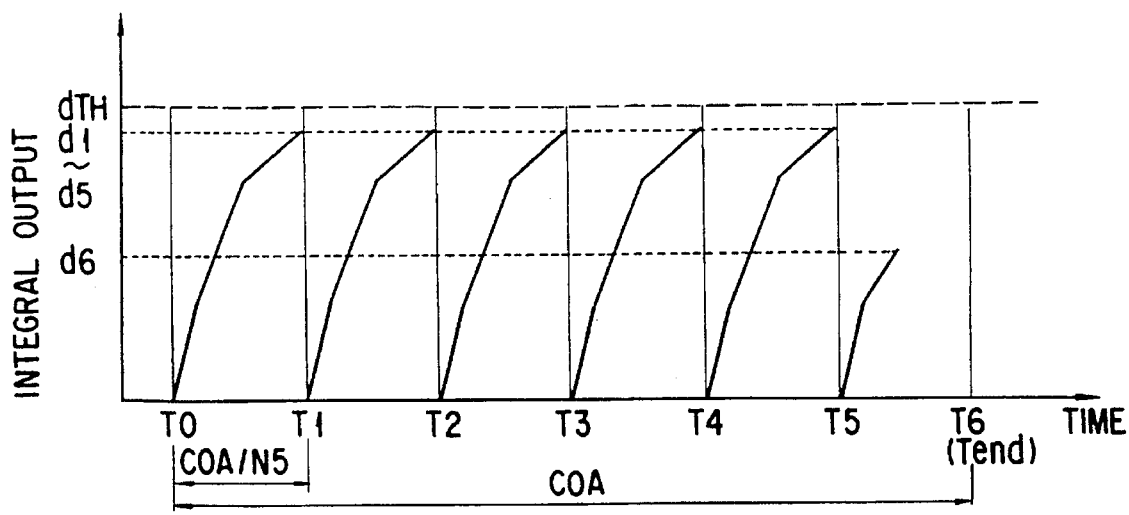
F I G. 18B
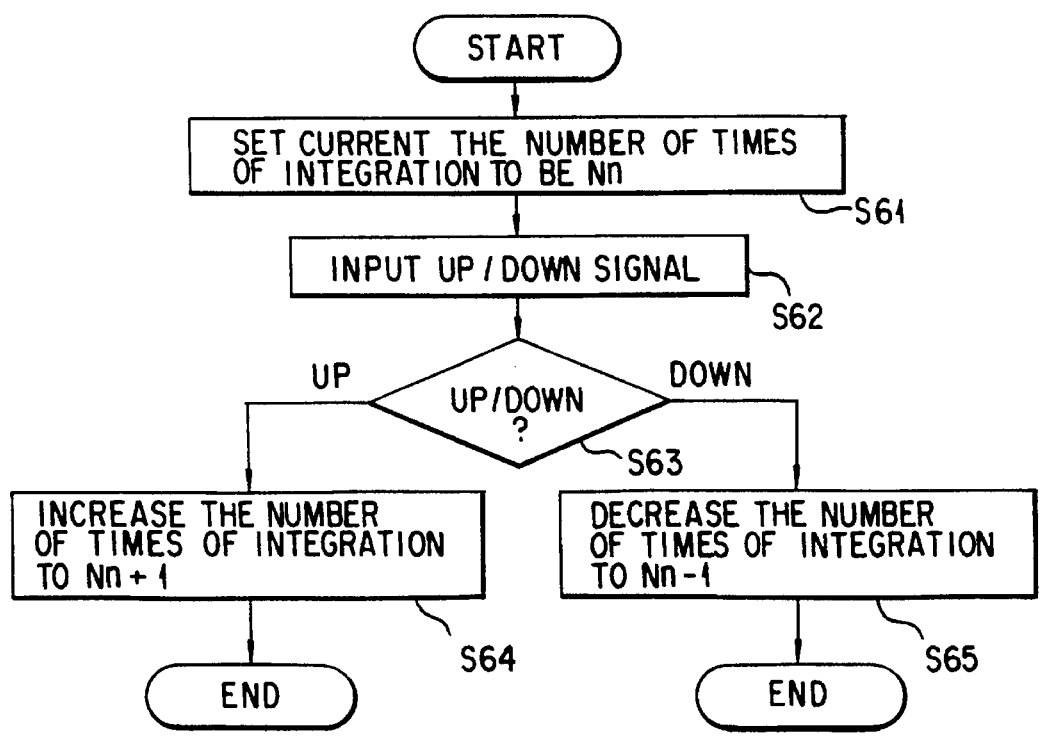
F I G. 20

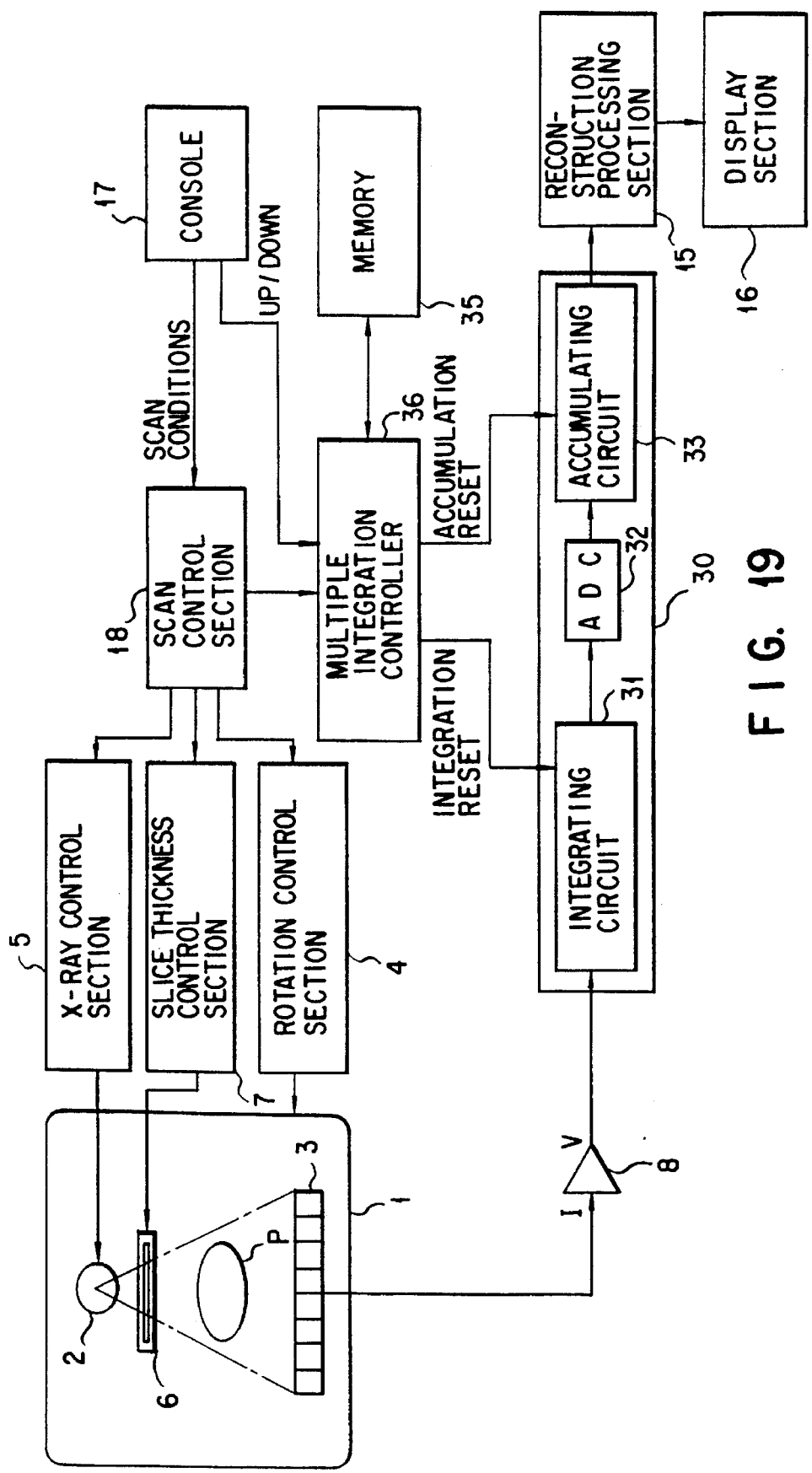
F I G. 19

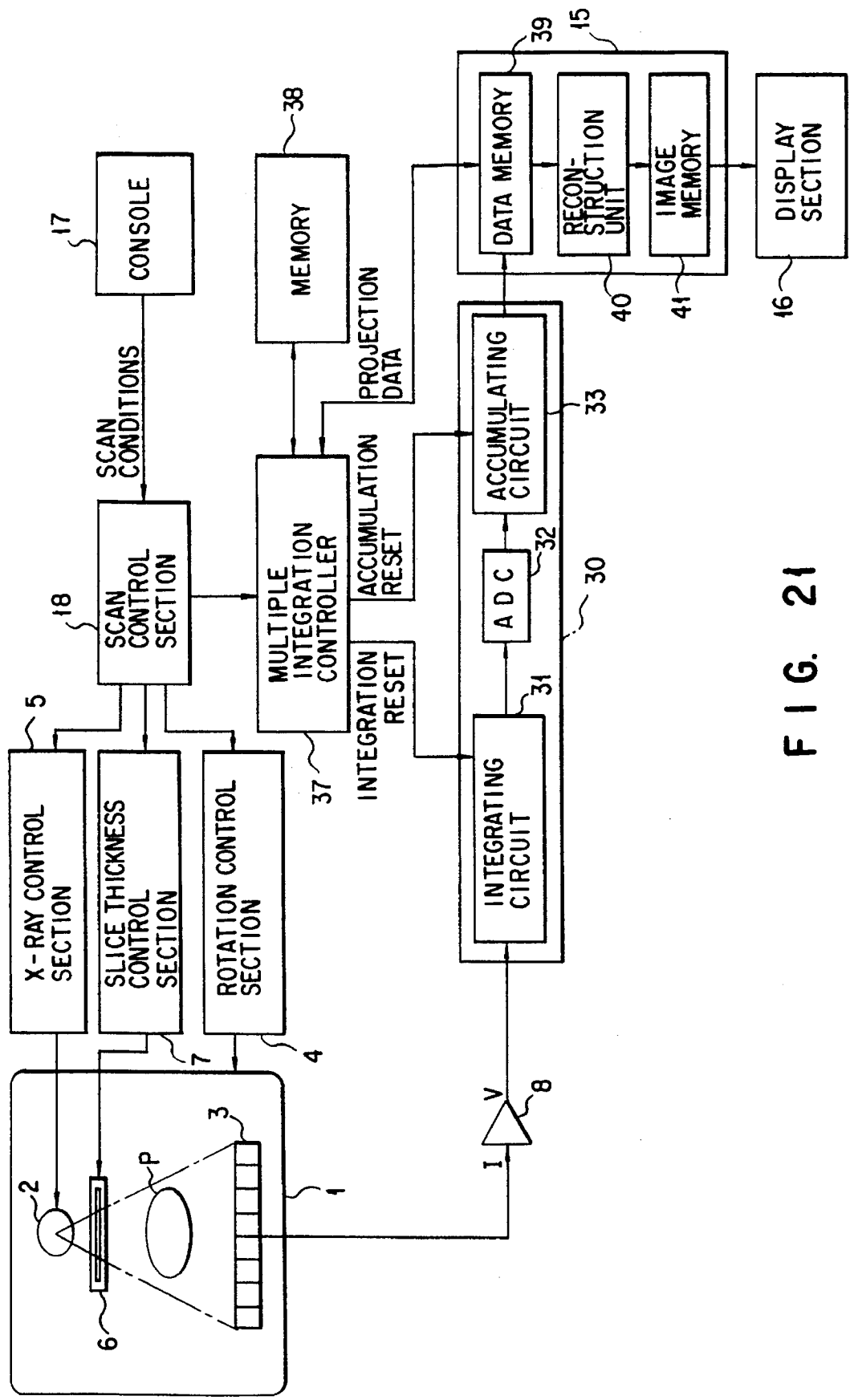
F I G. 21

X-RAY COMPUTED TOMOGRAPHY APPARATUS

BACKGROUND OF THE INVENTION

1. Field of the Invention

The present invention relates to an X-ray computer tomography apparatus (to be referred to as an X-ray CT hereinafter) for reconstructing a tomographic image on the basis of projection data obtained in many directions about an object to be examined.

2. Description of the Related Art

Image noise in an X-ray CT includes circuit noise and photon noise. Circuit noise becomes conspicuous when the dose of X-rays which are transmitted through an object to be examined and incident on an X-ray detector is relatively small, i.e., the data level is relatively low, but becomes latent when the dose of incident X-rays is relatively large. Photon noise is caused by fluctuations in the number of photons in incident X-rays, and is in inverse proportion to the square root of the number of photons. Therefore, the photon noise decreases in proportion to the dose of incident X-rays.

That is, the circuit noise in image noise becomes dominant when the dose of incident X-rays is relatively small, whereas the photon noise becomes dominant when the dose of incident X-rays is relatively large.

An oversampling method has been proposed as a method of reducing the circuit noise. Generally, in a data acquisition system (DAS), an output from an X-ray detector is integrated by an integrating circuit during an interval in which pulse X-rays are irradiated. The integral value at the end of this interval is converted into a digital signal by an analog/digital converter. The digital signal is then output, as projection data, to a computer system. In contrast to this, in an oversampling method, an output from the integrating circuit is sampled M times in the initial period of the above interval, and the M integral values are averaged. Similarly, in the oversampling method, an output from the integrating circuit is sampled M times in the final period of the above interval, and the M integral values are averaged. The average value obtained in the initial period is then subtracted from the average value obtained in the final period to obtain projection data. However, the integration interval in the oversampling method is substantially shortened to the interval between the time the integral output reaches the initial average value and the time the integral output reaches the final average value. As a result, the availability of X-rays substantially deteriorates. That is, there is a trade-off between a reduction in circuit noise and an improvement in the availability of X-rays, and these requirements cannot be satisfied at the same time.

The sensitivity of an X-ray detector, typically a semiconductor detector, has recently improved. In contrast to this, the broadening of the dynamic range of a DAS which is mainly dependent on the performance of an analog/digital converter is limited, and hence an overflow may occur. Therefore, for example, a polygonal line amplifier is connected to the input terminal of the analog/digital converter to decrease the gain from a proper voltage, thereby satisfying the above requirements. This, however, sacrifices the resolution.

SUMMARY OF THE INVENTION

It is an object of the present invention to provide an X-ray CT which can properly reduce circuit noise and suppress a deterioration in the availability of X-rays.

It is another object of the present invention to provide an X-ray CT which can prevent the occurrence of an overflow and allows a high resolution.

According to a first aspect of the invention, the following functions and effects can be achieved. Detection signals based on X-rays transmitted through an object to be examined are repeatedly integrated by the integrating means at predetermined intervals. The resultant integral signal is sampled a plurality of number of times in the initial period of the interval, and the sampled signals are averaged. The integral signal is also sampled a plurality of number of times in the final period of the interval, and the sampled signals are averaged. Projection data is created by subtracting the initial average value from the final average value. This method of creating projection data is called an oversampling scheme. According to this oversampling scheme, circuit noise can be reduced in accordance with the number of times of sampling. However, since the integration interval is substantially shortened, the X-ray availability deteriorates. The present invention is made on the basis of the characteristics that circuit noise becomes conspicuous when the dose of transmitted X-rays (equivalent to X-rays incident on a detection means) is relatively small, and becomes latent when the dose of X-rays is relatively large. The number of times of sampling is controlled by an oversampling control means on the basis of scan conditions which allow estimation of the dose of transmitted X-rays in such a manner. With this operation, when the dose of transmitted X-rays is relatively small, the circuit noise reducing effect can be improved at the cost of a deterioration in X-ray availability. When the dose of transmitted X-rays is relatively large, the X-ray availability can be improved.

According to a second aspect of the invention, the following functions and effects can be achieved. When information for increasing/decreasing the number of times of sampling is input by the operator via the input means, the number of times of sampling performed by the sampling means is increased/decreased by the oversampling control means. Therefore, when the dose of transmitted X-rays is relatively small, a circuit noise reducing effect can be improved at the cost of a deterioration in X-ray availability. When the dose of transmitted X-rays is relatively large, the X-ray availability can be improved.

According to a third aspect of the invention, the number of times of sampling is determined in accordance with the level of past projection data. With this operation, when the dose of transmitted X-rays is relatively small, the circuit noise reducing effect can be improved at the cost of a deterioration in X-ray availability. When the dose of transmitted X-rays is relatively large, the X-ray availability can be improved.

According to a fourth aspect of the invention, the following functions and effects can be achieved. Detection signals based on X-rays transmitted through an object to be examined are repeatedly integrated by the multiple integrating means within a predetermined interval. With this operation, an overflow can be prevented. In addition, the multiple integration control means controls the number of times of integration on the basis of scan conditions which allow estimation of the dose of transmitted X-rays. Therefore, when the dose of transmitted X-rays is relatively small, the number of times of integration is decreased. When the dose of transmitted X-rays is relatively large, the number of times of integration is increased. With this operation, an overflow can be prevented, and the number of times of integration can be minimized.

According to a fifth aspect of the invention, the following functions and effects can be achieved. When information for increasing/decreasing the number of times of integration is input by the operator via the input means, the number of times of integration performed by the multiple integrating means is increased/decreased by the multiple integration control means. Therefore, when the dose of transmitted X-rays is relatively small, the number of times of integration is decreased. When the dose of transmitted X-rays is relatively large, the number of times of integration is increased. With this operation, an overflow can be prevented, and the number of times of integration can be minimized.

According to a sixth aspect of the invention, the number of times of integration is determined in accordance with the level of past projection data. Therefore, when the dose of transmitted X-rays is relatively small, the number of times of integration is decreased. When the dose of transmitted X-rays is relatively large, the number of times of integration is increased. With this operation, an overflow can be prevented, and the number of times of integration can be minimized.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 11A and 11B are flow charts showing procedures employed by an oversampling controller in FIG. 10 to determine and set the number of times of sampling;

FIG. 13 is a graph showing the relationships between the incident doses and the numbers of times of integration which are stored in a memory in FIG. 12;

FIG. 14 is a flow chart showing a procedure for multiple integration;

FIGS. 18A and 18B are a timing chart and a graph showing the number of times of integration and an integration interval which are set when the incident dose is relatively large;

FIG. 19 is a block diagram showing the arrangement of the main part of an X-ray CT according to the fifth embodiment of the present invention;

FIG. 20 is a flow chart showing a procedure employed by a multiple integration controller in FIG. 19 to change the number of times of integration;

FIG. 21 is a block diagram showing the arrangement of the main part of an X-ray CT according to the sixth embodiment of the present invention.

DETAILED DESCRIPTION OF THE PREFERRED EMBODIMENTS

An X-ray CT according to an embodiment of the present invention will be described below with reference to the accompanying drawings.

(First Embodiment)

Figure 1:
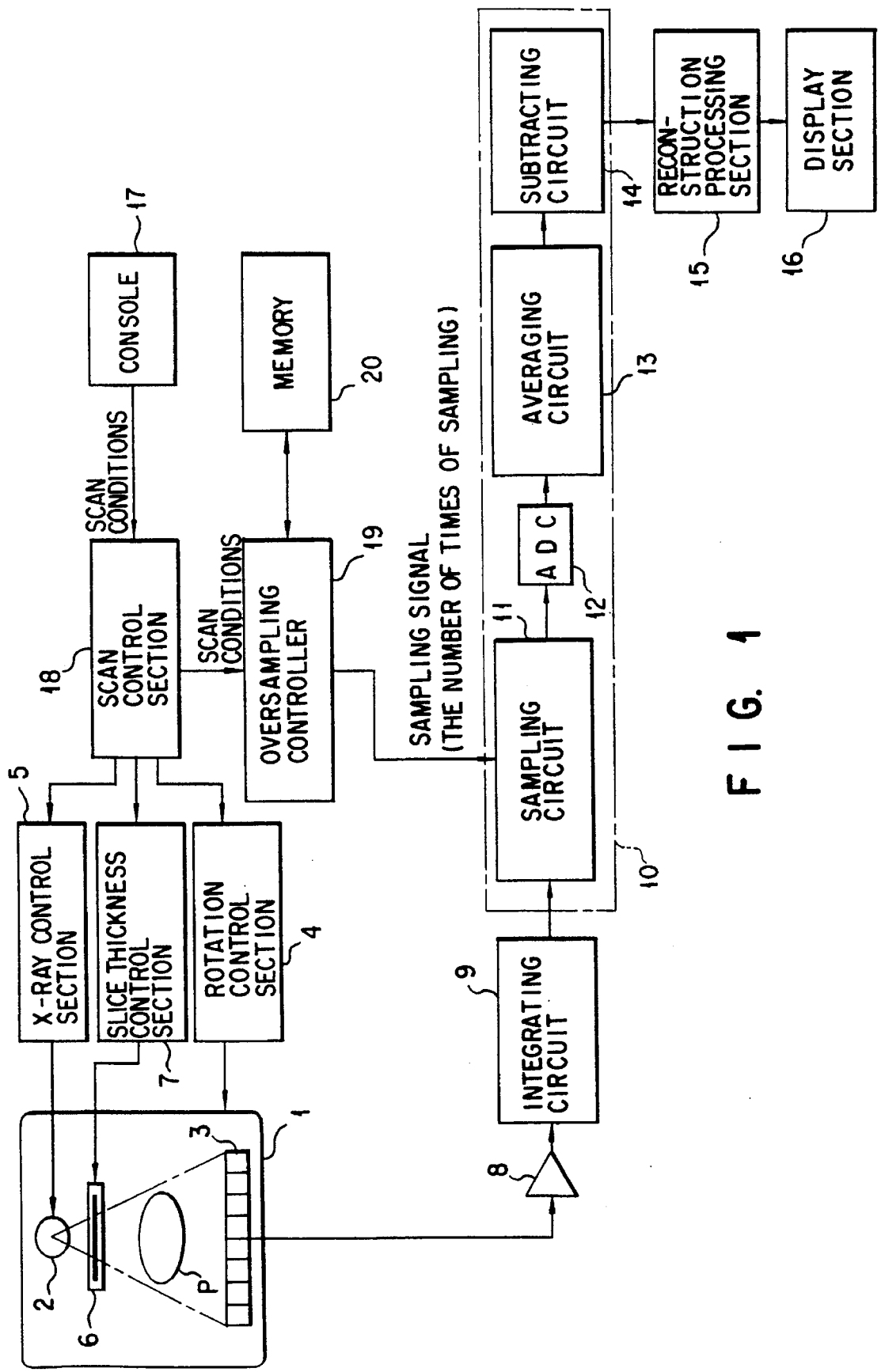
FIG. 1 is a block diagram showing the arrangement of the main part of an X-ray CT according to the first embodiment of the present invention.

FIG. 1 shows the arrangement of the main part of an X-ray CT according to the first embodiment. An X-ray tube 2 and an X-ray detector 3 are housed in a scanner body 1. If the scanner is of the third-generation R/R type, the X-ray tube 2 and the X-ray detector 3 are supported to be rotatable around an object P to be examined while they are kept opposing each other via the object P. The X-ray detector 3 has X-ray detection elements, each of which consists of a combination of a scintillator and a photodiode, and which are arranged in the form of an arc centered on the X-ray tube 2. If the scanner is of the fourth-generation R/S type, a large number of X-ray detection elements are fixed around the object P in the form of a circle, and the X-ray tube 2 is supported to be rotatable along the circumference of the circle. If the scanner is of the fifth-generation S/S type, large numbers of X-ray tube 2 and X-ray detection elements are fixed around the object P in the form of circles. Assume, in this case, that the scanner is of the third-generation R/R type. A rotation control section 4 controls the rotation of the X-ray tube 2 and the X-ray detector 3.

An X-ray control section 5 applies a high voltage (tube voltage) to the X-ray tube 2, together with a filament current (tube current), to cause the X-ray tube 2 to emit X-rays continuously or in the from of pulses. X-rays emitted from the X-ray tube 2 are collimated in the fan and slice directions via a variable collimator 6 and reach the object P. The variable collimator 6 has a plurality of movable lead plates to allow arbitrary changes in slice thickness. A slice thickness control section 7 controls the width of a slit formed by the movable lead plates of the rotation control section 4.

X-rays transmitted through the object P are incident on the X-ray detector 3. Each element of the X-ray detector 3 outputs a detection signal (current signal) corresponding to the dose of transmitted X-rays (equal to the dose of X-rays incident on the X-ray detector 3). These detection signals are amplified and voltage-converted by a preamplifier 8 in units of channels. The resultant data is then repeatedly integrated by an integrating circuit 9 at predetermined data acquisition intervals. The integral signal from the integrating circuit 9 is sent to an oversampling circuit 10.

The oversampling circuit 10 creates projection data by an oversampling scheme on the basis of the integral signal from the integrating circuit 9. One projection data is created per data acquisition interval. The oversampling circuit 10 comprises a sampling circuit 11, an analog/digital converter (ADC) 12, an averaging circuit 13, and a subtracting circuit 14. The sampling circuit 11 repeatedly samples the integral signal from the integrating circuit 9 a plurality of number of times (M times) in the initial period of a data acquisition interval, and repeatedly samples the integral signal from the integrating circuit 9 M times in the final period of the data acquisition interval. The analog/digital converter 12 converts a signal voltage, sampled by the sampling circuit 11, into a digital signal. The averaging circuit 13 averages the M digital signals sampled by the sampling circuit 11 in the initial period to obtain an initial average value, and also averages the M digital signal sampled in the final period to obtain a final average value. The subtracting circuit 14 subtracts the initial average value from the final average value, obtained by the averaging circuit 13, so as to create projection data.

The sampling circuit 11 is designed to change the number of times of sampling. More specifically, the sampling circuit 11 repeats sampling at predetermined sampling intervals mainly determined by the operating speed of the analog/digital converter 12 while a sampling signal is supplied from an oversampling controller 19. That is, the number of times of sampling increases/decreases in accordance with the duration of a sampling signal supplied from the oversampling controller 19 to the sampling circuit 11. Therefore, the oversampling controller 19 adjusts the sampling interval by changing the duration of a sampling signal, thereby increasing/decreasing the number of times of sampling.

The projection data created by the oversampling circuit 10 is supplied to a reconstruction processing section 15. The reconstruction processing section 15 reconstructs one tomographic image on the basis of projection data corresponding to one rotation (360°). This tomographic image is visually displayed on a display section 16.

Scan conditions including a tube voltage, a tube current, a scan time, a slice thickness, and a reconstruction area and a scan start/end command are input through a console 17. A scan is defined as a unit operation of acquiring projection data corresponding to, e.g., one rotation (360°) which is required to reconstruct one tomographic image. The scan time required for one scan is almost equal to the time required for one rotation (360°) of the X-ray tube 2 and the like. The reconstruction area is generally a circular area which is set to increase the reconstruction calculation speed by eliminating calculations in unnecessary areas. The size of this area is input as a diameter.

A scan control section 18 controls the slice thickness control section 7 to realize an input slice thickness. The scan control section 18 transfers scan time information and tube voltage/tube current information to the rotation control section 4 and the X-ray control section 5, respectively. The scan control section 18 also transfers the scan conditions to the oversampling controller 19. In response to a scan start command, the scan control section 18 supplies a scan start signal to the rotation control section 4, the X-ray control section 5, the integrating circuit 9, and the oversampling circuit 10. The rotation control section 4 starts to rotate the X-ray tube 2 and the like at the reception timing of the scan start signal. Thereafter, the rotation control section 4 controls the scanner body 1 to rotate the X-ray tube 2 and the like at a constant angular velocity which realizes the scan time. The X-ray control section 5 starts to supply a set tube voltage and tube current to the X-ray tube 2 at the timing when the X-ray tube 2 and the like reach the constant velocity. The integrating circuit 9 repeatedly integrates detection signals from the X-ray detector 3 at predetermined data acquisition intervals set by the scan control section 18. The oversampling controller 19 supplies sampling signals to the sampling circuit 11 at the respective timings of the initial and final periods of each data acquisition interval.

Figure 2:
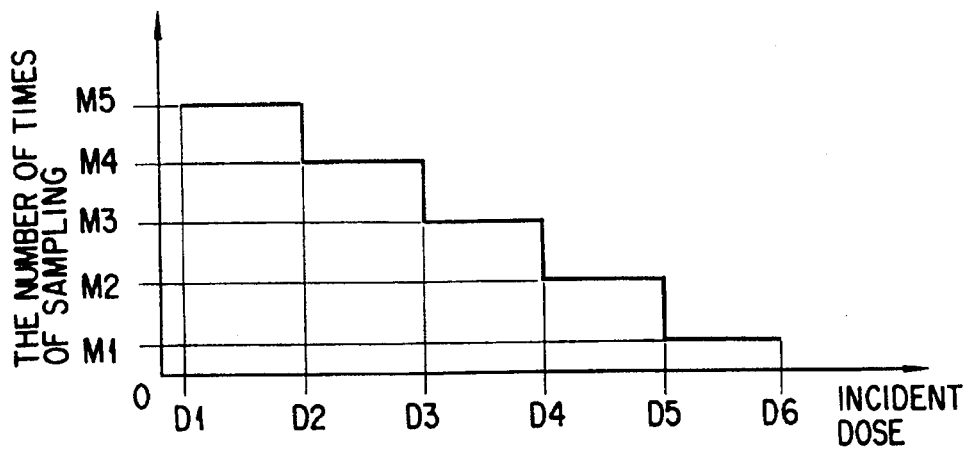
FIG. 2 is a graph showing the relationships between the incident doses and the numbers of times of sampling which are stored in a memory in FIG. 1.

In a memory 20 connected to the oversampling controller 19, incident doses measured by using phantoms and the like in advance are stored in correspondence with various scan conditions, and optimal numbers of times of sampling are also stored in correspondence with various incident doses. A relatively large number of times of sampling corresponds to a relatively small incident dose. With an increase in incident dose, the corresponding number of times of sampling gradually decreases. FIG. 2 shows an example of the relationship between the incident dose and the number of times of sampling. For example, a number M4 of times of sampling is given as an optimal value for the incident doses in the range from D2 to D3. As is apparent, the memory 20 may directly store various relationships between the scan conditions and the numbers of times of sampling.

If the diameter of a reconstruction area is regarded as the length of the path of X-rays passing through the object P, the dose of X-rays incident on the X-ray detector 3 can be obtained on the basis of the tube voltage, the tube current, and the slice thickness as well as this reconstruction area. The oversampling controller 19 obtains an incident dose on the basis of the reconstruction area, the tube voltage, the tube current, and the slice thickness in the scan conditions supplied from the scan control section 18. More specifically, the oversampling controller 19 forms an address on the basis of the reconstruction area, the tube voltage, the tube current, and the slice thickness, and accesses the memory 20 in accordance with this address, thereby obtaining incident dose data. The oversampling controller 19 obtains an optimal number of times of sampling on the basis of the incident dose. More specifically, the oversampling controller 19 forms an address on the basis of the incident dose, and accesses the memory 20 in accordance with this address, thereby obtaining optimal number-of-times-of-sampling data.

Figure 3:
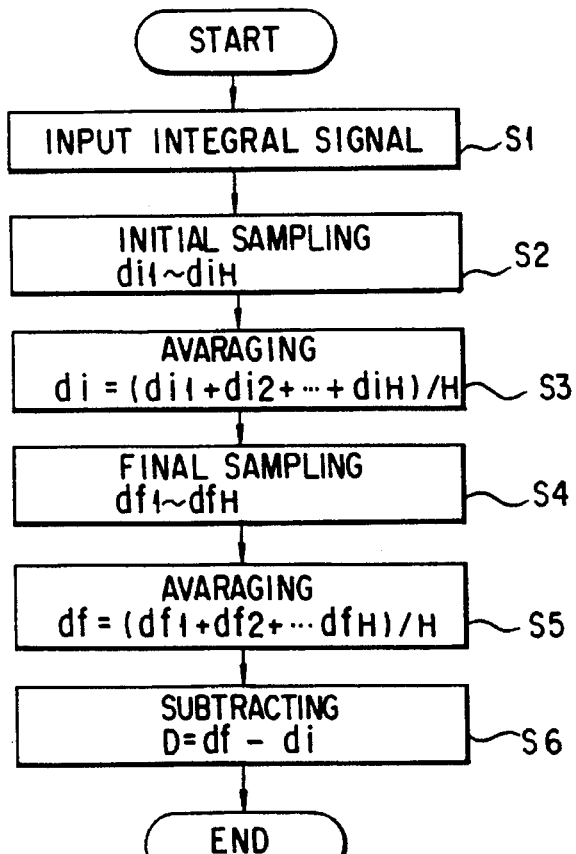
FIG. 3 is a flow chart showing a procedure for oversampling.
Figure 4A:
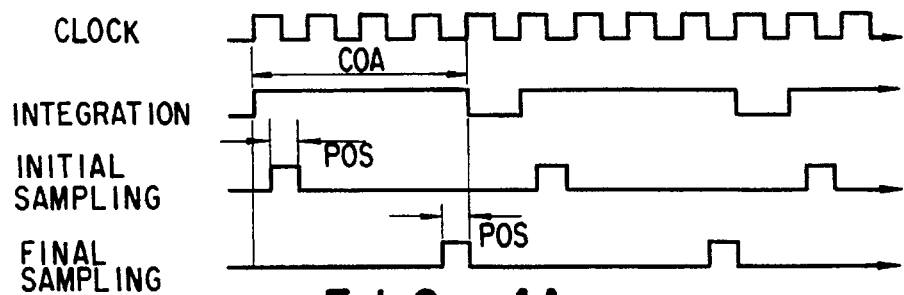
FIGS. 4A to 4C are timing charts and a graph for explaining an oversampling operation.
Figure 4B:
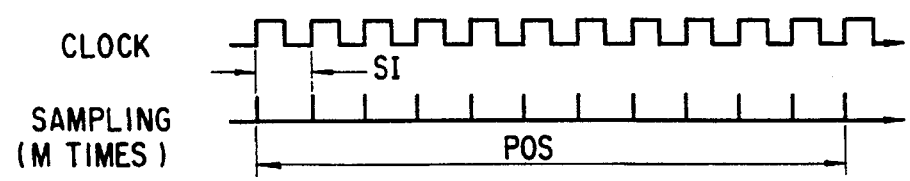
Figure 4C:
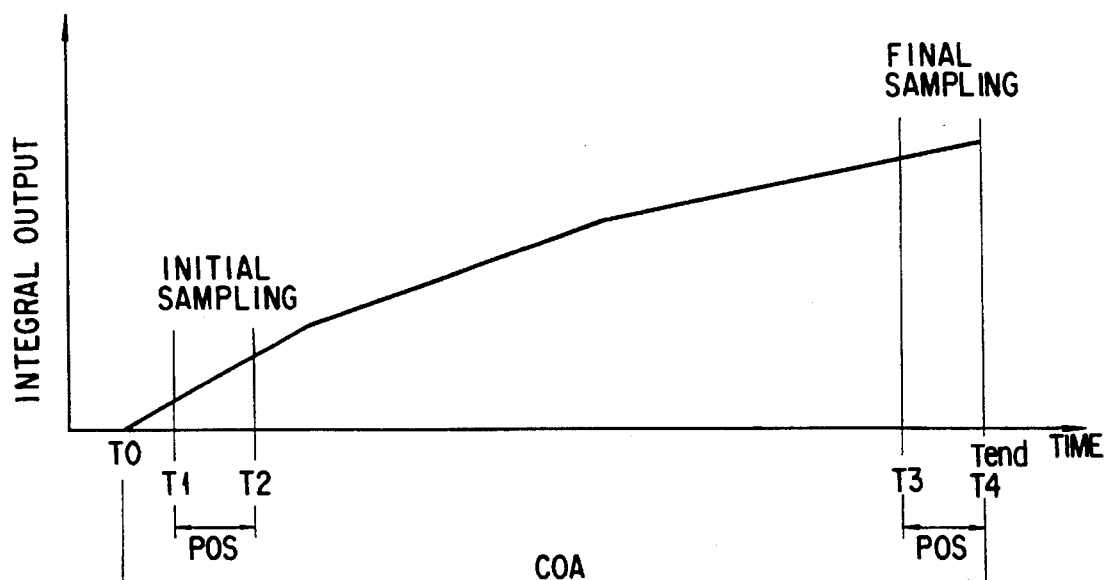

FIG. 3 is a flow chart showing a procedure for an oversampling operation performed by the oversampling circuit 10. FIG. 4A is a timing chart showing the relationship in time between the integrating operation of the integrating circuit 9 and the sampling operation of the sampling circuit 11. FIG. 4B is a timing chart showing a sampling operation in detail. FIG. 4C is a graph showing the time waveform of an integral signal in a given data acquisition interval. Detection signals detected by the X-ray detector 3 are supplied to the integrating circuit 9 via the preamplifier 8 to be integrated with respect to time. The integral signal is reset to "0" at data acquisition intervals COA. The integral signal from the integrating circuit 9 is input to the sampling circuit 11 (step S1). The integral signal is repeatedly sampled M times at predetermined sampling intervals SI in an interval POS (between time T1 to time T2) in which an initial sampling signal is supplied from the oversampling controller 19 to the sampling circuit 11 (step S2). Note that the initial sampling signal is preferably supplied after the lapse of a predetermined delay time from the start point of the data acquisition interval COA so as to compensate for a transient response error and a zero reset error. M series-sampled signals are converted into digital signals di1 to dim by the ADC 12 and held in, e.g., a register of the averaging circuit 13. The averaging circuit 13 averages these digital signals to obtain an initial average value di (step S3). This initial average value di is stored in, e.g., a register of the subtracting circuit 14. In addition, the integral signal from the integrating circuit 9 is repeatedly sampled M times at the predetermined sampling intervals SI in an interval POS in which a final sampling signal is supplied from the oversampling controller 19 to the sampling circuit 11 (step S4). Note that the end point of the final sampling signal is set to coincide with an end point Tend of the data acquisition interval COA so as to improve the X-ray availability. M series-sampled signals are converted into digital signals df1 to dfM by the ADC 12 and stored in, e.g., a register of the averaging circuit 13. The averaging circuit 13 averages the digital signals df1 to dfM to obtain a final average value df (step S5). This final average value df is stored in, e.g., a register of the subtracting circuit 14. The subtracting circuit 14 then subtracts the initial average value di from the final average value df to create projection data D (step S6). Such an oversampling operation is performed for each channel.

Circuit noise can be reduced by oversampling. On the other hand, since the substantial integration interval is shortened to the interval between the time the integral signal reaches the initial average value and the time the integral signal reaches the final average value, the X-ray availability deteriorates.

In this embodiment, in order to cope with such a conflict between a reduction in circuit noise and a deterioration in X-ray availability, the number of times of sampling (sampling interval) is increased/decreased in accordance with the incident dose. When the incident dose is small, since the circuit noise becomes conspicuous, the number of times of sampling is increased at the cost of a deterioration in X-ray availability. When the incident dose is relatively large, since the circuit noise becomes latent, the number of times of sampling is decreased to improve the X-ray availability.

Figure 5:
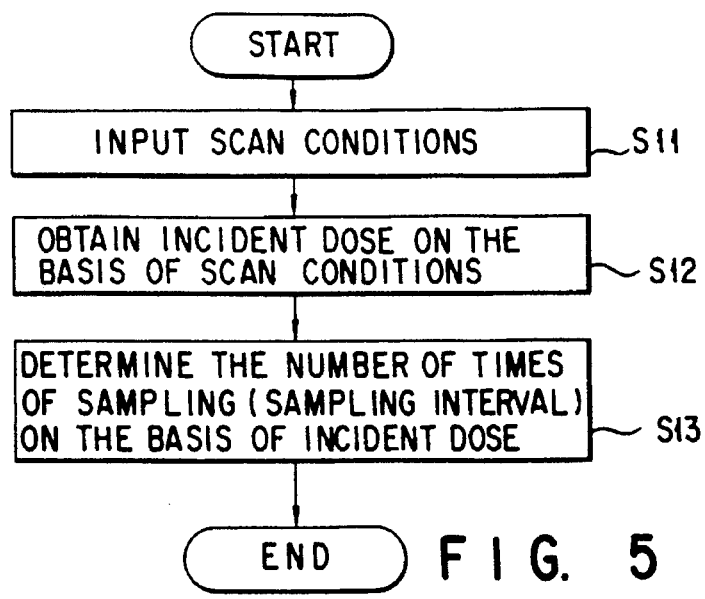
FIG. 5 is a flow chart showing a procedure employed by an oversampling controller in FIG. 1 to determine the number of times of sampling.

FIG. 5 is a flow chart showing a procedure employed by the oversampling controller 19 to determine the number of times of sampling. Scan conditions including a reconstruction area, a tube voltage, a tube current, and a slice thickness are supplied from the scan control section 18 to the oversampling controller 19 (step S11). The reconstruction area, the tube voltage, the tube current, and the slice thickness which are required to obtain an incident dose are extracted from the scan conditions by the oversampling controller 19.

An incident dose is then obtained on the basis of these extracted conditions (step S12). More specifically, an address is formed on the basis of the extracted conditions, and incident dose data is sent from the memory 20 to the oversampling controller 19. In addition, the oversampling controller 19 obtains an optimal number of times of sampling on the basis of the incident dose (step S13). More specifically, an address is formed on the basis of the incident dose, and number-of-times-of-sampling data is sent from the memory 20 to the oversampling controller 19.

Figure 6A:
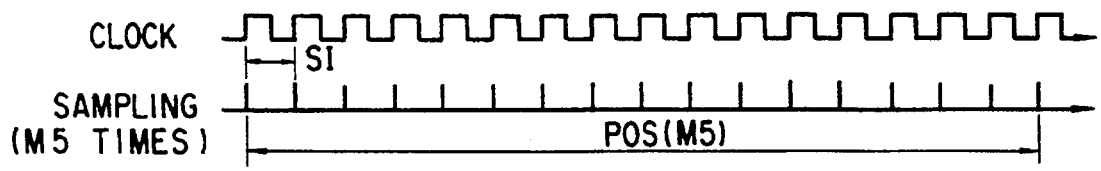
FIGS. 6A and 6B are a timing chart and a graph showing the number of times of sampling and an interval which are set when the incident dose is relatively small.
Figure 6B:
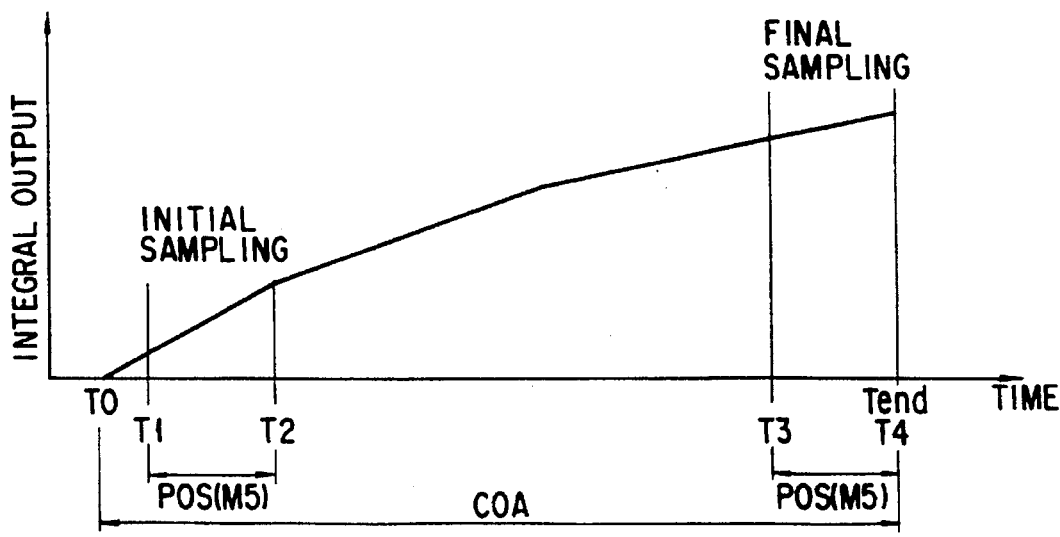
Figure 7A:
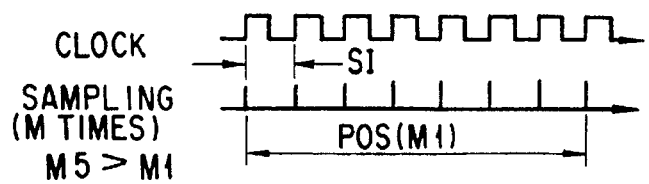
FIGS. 7A and 7B are a timing chart and a graph showing the number of times of sampling and an interval which are set when the incident dose is relatively large.
Figure 7B:
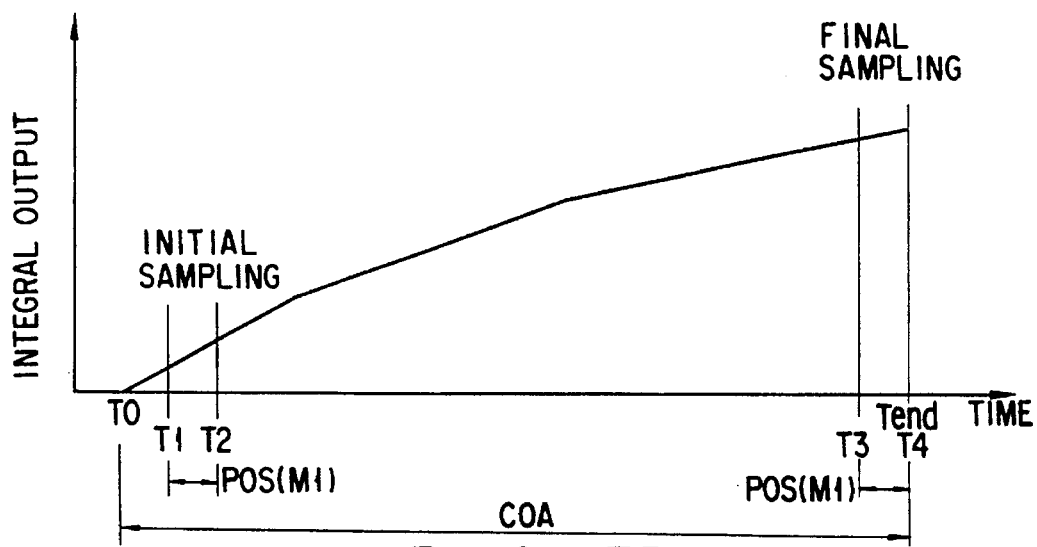

The oversampling controller 19 obtains a duration of a sampling signal in accordance with the obtained number M of times of sampling according to "Si×M". Sampling is then performed the optimal number M of times by supplying the sampling signal to the sampling circuit 11 for this duration. FIGS. 6A and 6B respectively show the number of times of sampling and a sampling interval which are set when the incident dose is a relatively small dose falling within the range from D1 to D2 in FIG. 2. FIGS. 7A and 7B show the number of times of sampling and a sampling interval which are set when the incident dose is a relatively large dose falling within the range from D5 to D6 in FIG. 2.

When the incident dose is relatively small, the sampling interval POS is prolonged, and the number M of time of sampling is increased. The circuit noise is reduced to $1/\sqrt{M}$ with respect to the number M of times of sampling. Therefore, the circuit noise reducing effect improves, and the S/N ratio increases.

When the incident dose is relatively large, the sampling period POS is shortened, and the number of times of sampling is decreased. As a result, the substantial integration interval becomes closer to the data acquisition interval COA, and the X-ray availability improved. In this case, as the number of times of sampling decreases, the circuit noise reducing effect deteriorates. When the incident dose is relatively large, the amplitude of a detection signal increases accordingly. In contrast to this, the circuit noise does not change regardless of an increase/decrease in incident dose. Therefore, when the incident dose is relatively high, since the circuit noise is latent, the high S/N ratio is maintained, even if the number of times of sampling is decreased.

(Second Embodiment)

In the second embodiment, similar to the first embodiment, the number of times of sampling is determined on the basis of scan conditions according to a procedure like the one shown in FIG. 5. This embodiment is characterized in that the current number of times of sampling (determined number of times of sampling) is manually increased/decreased in accordance with an instruction from the operator.

Figure 8:
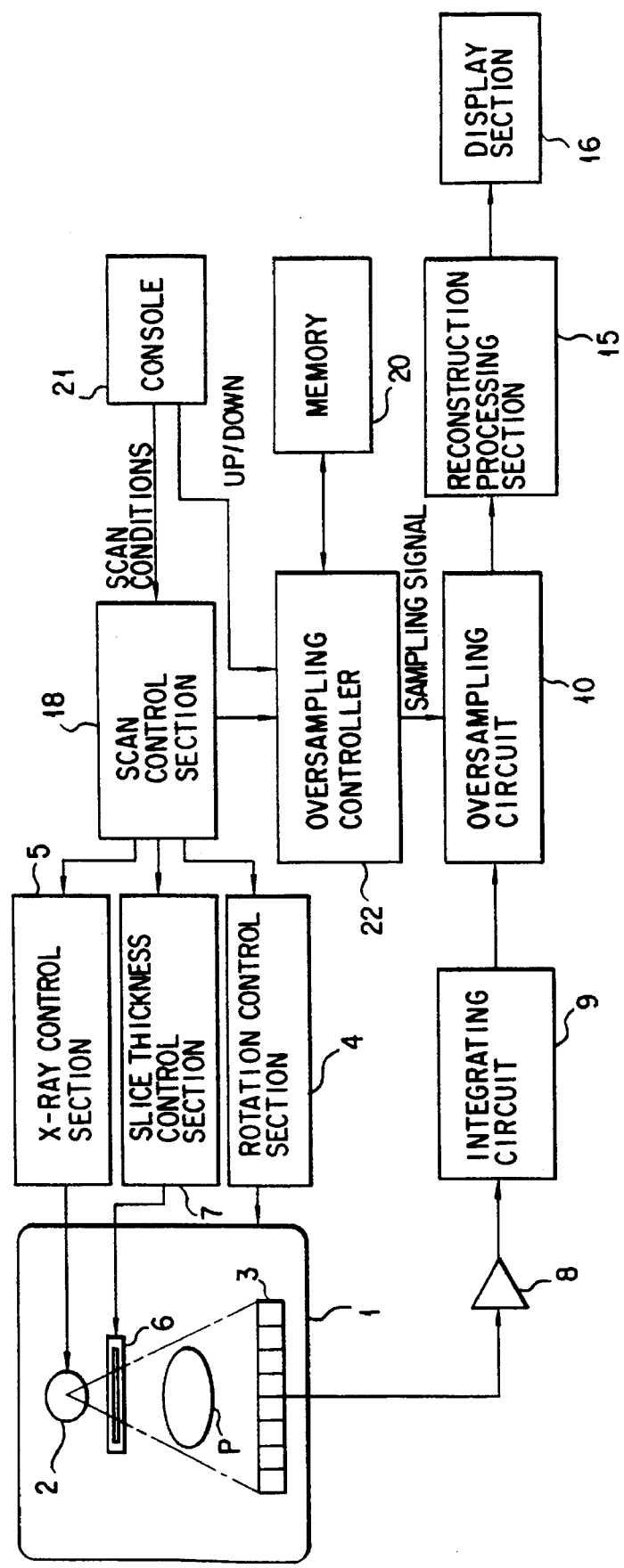
FIG. 8 is a block diagram showing the arrangement of the main part of an X-ray CT according to the second embodiment of the present invention.

FIG. 8 shows the arrangement of the main part of an X-ray CT according to the second embodiment. The same reference numerals in FIG. 8 denote the same parts as in FIG. 1, and a description thereof will be omitted. A console 21 includes a key or switch used by the operator to issue a command (UP/DOWN command) for increasing/decreasing the number of times of sampling, in addition to keys or switches for inputting scan conditions and a scan start/end command as in the first embodiment. An oversampling controller 22 determines the number of times of sampling on the basis of scan conditions in the same manner as in the first embodiment, and controls a sampling circuit 11 to execute oversampling according to the determined number of times of sampling. Upon receiving an UP/DOWN command for increasing/decreasing the number of times of sampling via the console 21, the oversampling controller 22 increases/decreases the current number of times of sampling in accordance with this command and controls the sampling circuit 11 to execute oversampling according to the increased/decreased number of times of sampling.

Figure 9:
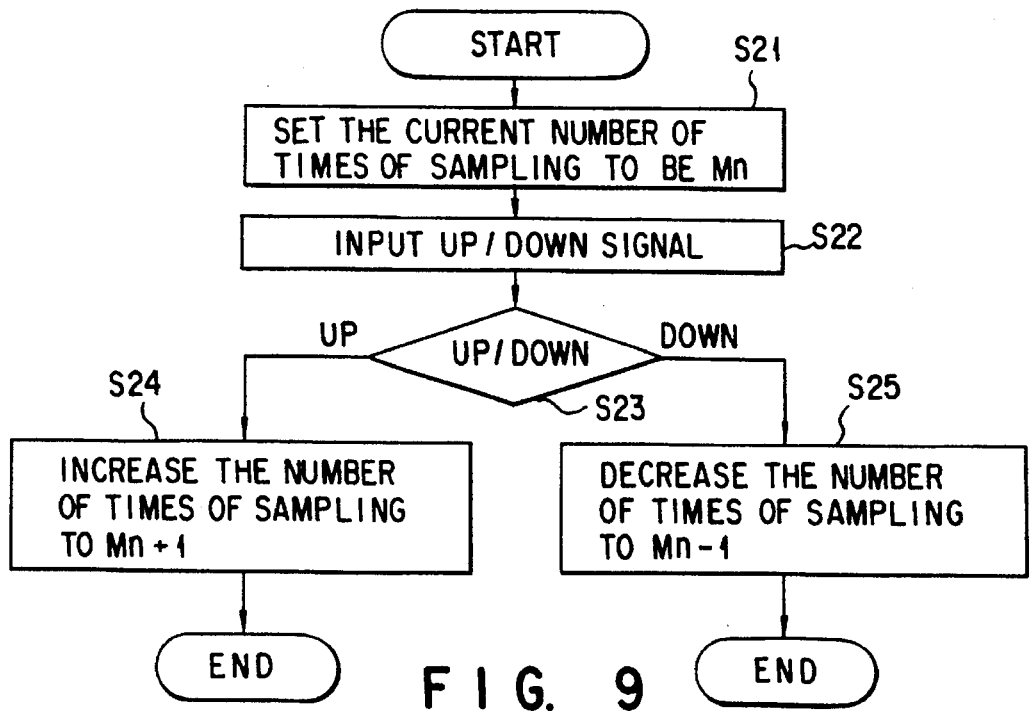
FIG. 9 is a flow chart showing a procedure employed by an oversampling controller in FIG. 8 to change the number of times of sampling.

FIG. 9 is a flow chart showing a procedure employed by the oversampling controller 22 to increase/decrease the number of times of sampling. First of all, let Mn be the current number of times of sampling (step S21). A signal (UP signal) for increasing the number of times of sampling or a signal (DOWN signal) for decreasing the number of times of sampling is supplied to the oversampling controller 22 via the console 21 (step S22). If it is determined in step S23 that the supplied signal is an UP signal, the current number Mn of times of sampling is increased to a number Mn+1 of times (step S24). If the current number of times of sampling is M3 in FIG. 2, the number M3 of times is increased by one step to M4. If the supplied signal is a DOWN signal, the current number Mn of times of sampling is decreased to Mn−1 (step S25). If, for example, the current number of times of sampling is M3, the number M3 of times is decreased by one step to M2.

As described above, according to this embodiment, the number of times of sampling can be manually increased/decreased by the operator.

(Third Embodiment)

The third embodiment is characterized in that the number of times of sampling is optimized for each projection angle on the basis of past projection data which has already been acquired.

Figure 10:
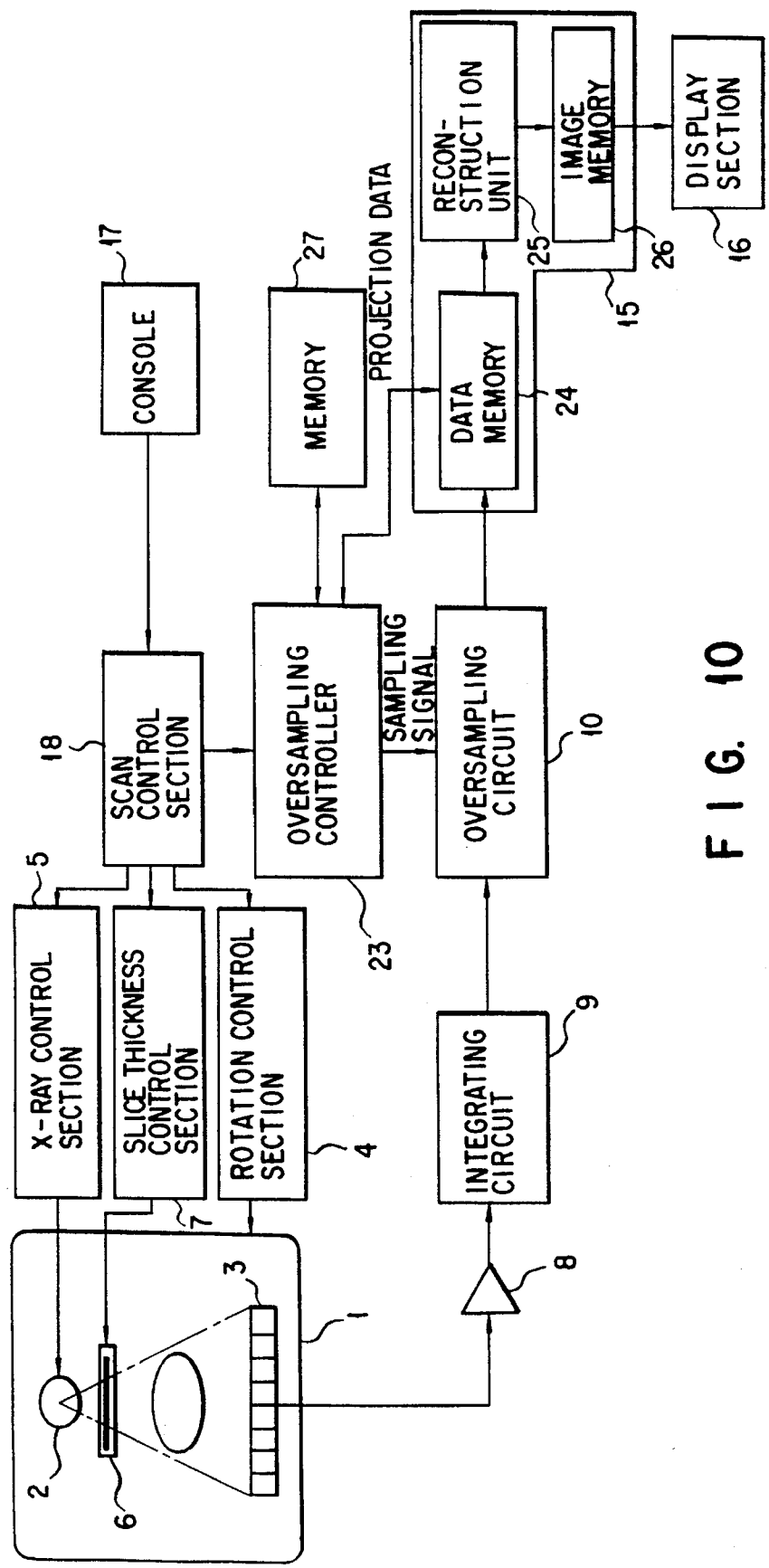
FIG. 10 is a block diagram showing the arrangement of the main part of an X-ray CT according to the third embodiment of the present invention.

FIG. 10 shows the arrangement of the main part of an X-ray CT according to the third embodiment. The same reference numerals in FIG. 10 denote the same parts as in FIG. 1, and a description thereof will be omitted. A reconstruction processing section 15 comprises a data memory 24, a reconstruction unit 25, and an image memory 26. Projection data created by an oversampling circuit 10 are stored in the data memory 24 at addresses corresponding to scan numbers, channel numbers, and the rotational angles (projection angles) of an X-ray tube 2. The reconstruction unit 25 reconstructs a tomographic image on the basis of projection data having the same scan number and corresponding to, e.g., one rotation. The image memory 26 temporarily stores a tomographic image and outputs it to a display section 16.

FIG. 11A is a flow chart showing a procedure employed by a multiple oversampling controller 23 in a method of determining the number of times of sampling. First of all, the multiple oversampling controller 23 accesses the data memory 24 to input projection data corresponding to a past scan number, preferably an immediately preceding scan number n−1, a rotational angle α, and a center channel number (step S31).

The multiple oversampling controller 23 accesses a memory 27 in accordance with this projection data to input an optimal number Mn of times of sampling which corresponds to the projection data (step S32). Similar to the case shown in FIG. 2, optimal numbers of times of sampling are stored in the memory 27 in correspondence with various projection data. A large number of times of sampling is caused to correspond to projection data of a relatively low level. With an increase in the level of projection data, the corresponding number of times of sampling gradually decreases.

The multiple oversampling controller 23 obtains a duration of a sampling signal by multiplying the number Mn of times of sampling by a sampling interval. The multiple oversampling controller 23 realizes the optimal number of times of sampling by supplying the sampling signal to a sampling circuit 11 for the obtained duration with respect to integral signals, in all the channels, which are detected when the X-ray tube 2 is at the rotational angle α in the current nth scan (step S34).

Such optimization of the number of times of sampling is repeated every time the rotational angle (projection angle) of the X-ray tube 2 changes.

According to this embodiment, the number of times of sampling can be optimized for each projection angle on the basis of past projection data.

This embodiment can be modified as follows. FIG. 11B is a flow chart showing a procedure in a modified method of determining the number of times of sampling. First of all, the multiple oversampling controller 23 accesses the data memory 24 to input projection data corresponding to a past scan number, preferably an immediately preceding number n−1, a rotational angle α, and the channel number of a channel CHi (step S41).

The multiple oversampling controller 23 then accesses the memory 27 in accordance with this projection data to input an optimal number Mn of times of sampling which corresponds to the projection data (step S42).

The multiple oversampling controller 23 obtains a duration of a sampling signal by multiplying the number Mn of times of sampling by a sampling interval. The multiple oversampling controller 23 realizes the optimal number of times of sampling by supplying the sampling signal to the sampling circuit 11 for the obtained duration with respect to an integral signal, in the channel CHi, which is detected when the X-ray tube 2 is at the rotational angle α in the current nth scan (step S44).

Such optimization of the number of times of sampling is performed for each channel.

According to this modification, the number of times of sampling can be optimized for each channel and each projection angle on the basis of past projection data.

(Fourth Embodiment)

Figure 12:
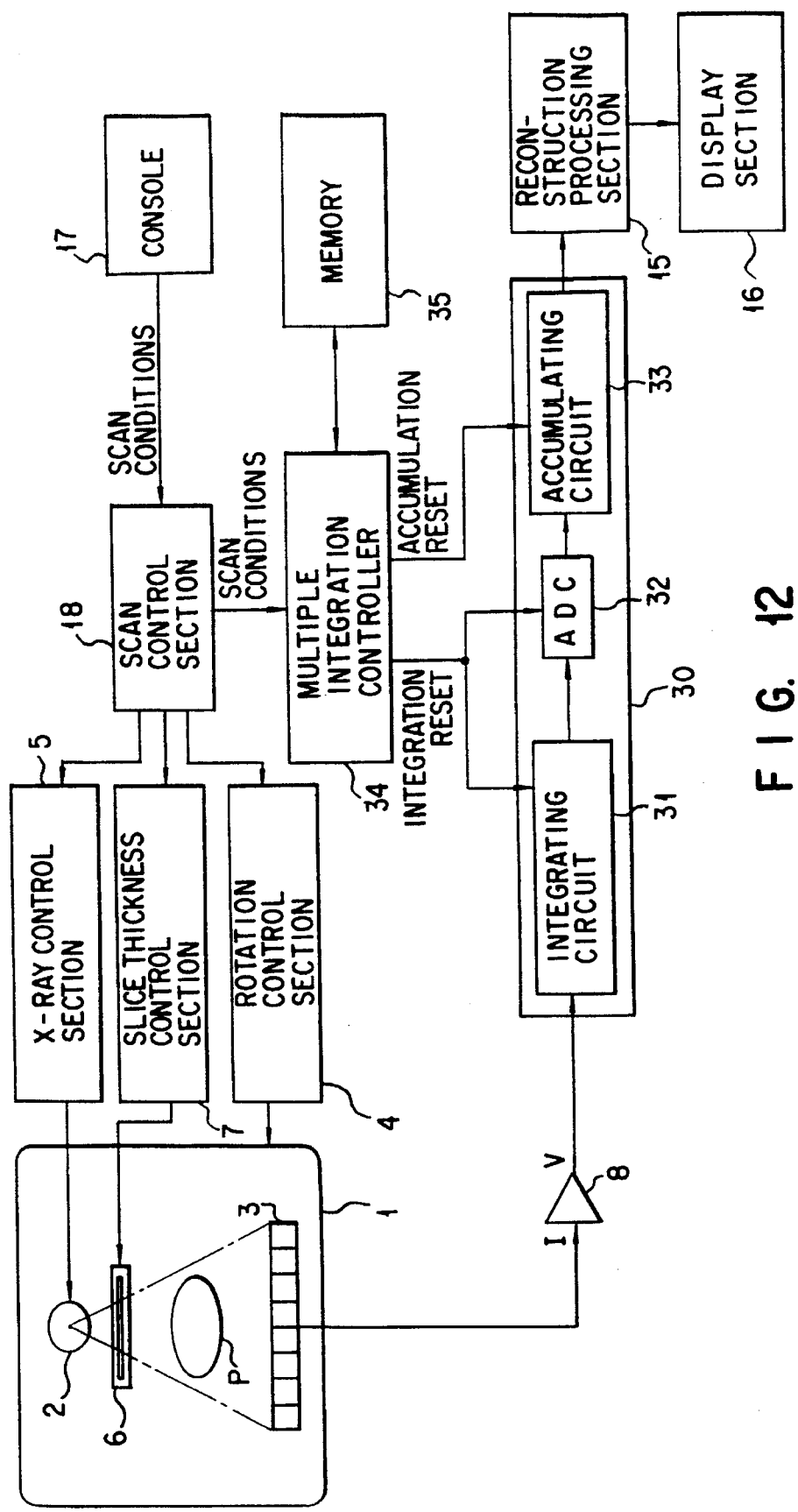
FIG. 12 is a block diagram showing the arrangement of the main part of an X-ray CT according to the fourth embodiment of the present invention.

FIG. 12 shows the arrangement of the main part of an X-ray CT according to the fourth embodiment. The same reference numerals in FIG. 12 denote the same parts as in FIG. 1, and a description thereof will be omitted. It is an object of the fourth embodiment to prevent an overflow.

Current signals (detection signal) output from the respective element of an X-ray detector 3 are amplified and voltage-converted by a preamplior 8 in units of channels. The signals are then supplied to a multiple integrating circuit 30. The multiple integrating circuit 30 creates projection data by a multiple integration scheme on the basis of the detected signals. The multiple integrating circuit 30 comprises an integrating circuit 31, an analog/digital converter (ADC) 32, and an accumulating circuit 33. The integrating circuit 31 integrates the detection signals from the preamplifier 8. An integration reset signal is supplied from a multiple integration controller 34 to the integrating circuit 31 a plurality of number of times during one data acquisition interval COA. Upon reception of the integration reset signal, the integrating circuit 31 resets the integral signal to "0", and resumes integration from the zero value. The integration reset signal is also supplied to the analog/digital converter 32. The analog/digital converter 32 converts an integral signal (voltage value) corresponding to the reception timing of the integration reset signal into a digital signal, and supplies it to the accumulating circuit 33. The accumulating circuit 33 creates projection data by accumulating a plurality of digital signals (updating held data to an algebraic sum) supplied from the analog/digital converter 32 during the same data acquisition interval COA. Upon receiving an accumulation reset signal from the multiple integration controller 34, the accumulating circuit 33 resets the cumulative value to "0", and prepares for the creation of the next projection data.

The projection data created by the multiple integrating circuit 30 is supplied to a reconstruction processing section 15. The reconstruction processing section 15 reconstructs one tomographic image on the basis of projection data corresponding to, e.g., one rotation (360×). This tomographic image is visually displayed on a display section 16.

In a memory 35, incident doses measured by using phantoms and the like in advance are stored in correspondence with various scan conditions, and optimal numbers of times of integration are also stored in correspondence with various incident doses. A relatively small number of times of integration corresponds to a relatively small incident dose. With an increase in incident dose, the corresponding number of times of integration gradually increases.

More specifically, a plurality of incident dose data are stored in the memory 35 at addresses corresponding to combinations of reconstruction areas, tube voltages, tube currents, and slice thicknesses which are required to obtain incident doses. In addition, a plurality of number-of-times-of-integration data are respectively stored at addresses corresponding to the incident doses. FIG. 13 shows an example of the relationships between incident doses D and the numbers of times of integration. For example, a number M4 of times of integration is given as an optimal value for the incident doses in the range from D2 to D3. As is apparent, in the memory 35, the optimal numbers of times of integration may be caused to directly correspond to various scan conditions, respectively.

The multiple integration controller 34 obtains an incident dose on the basis of a reconstruction area, a tube voltage, a tube current, and a slice thickness in scan conditions supplied from a scan control section 18, and determines an optimal number Nn of times of integration on the basis of this incident dose. More specifically, the multiple integration controller 34 produces an address on the basis of the reconstruction area, the tube voltage, the tube current, and the slice thickness in the scan condition, and accesses the memory 35 in accordance with this address, thereby obtaining incident dose data. In addition, the multiple integration controller 34 produces an address on the basis of the incident dose data, and accesses the memory 35 in accordance with this address, thereby obtaining the optimal number-of-times-of-integration data, for the incident dose in the above conditions, which causes no overflow and represents the minimum number of times.

The multiple integration controller 34 controls the integration interval set in the integrating circuit 31 in accordance with the number Nn of times of integration. More specifically, the multiple integration controller 34 obtains an integration interval as an interval COA/Nn in accordance with the number Nn of times of integration. The multiple integration controller 34 supplies an integration reset signal to the integrating circuit 31 and the analog/digital converter 32, from the beginning of the data acquisition interval COA, Nn times at the integration intervals COA/Nn obtained above. With this operation, detection signals detected during one data acquisition interval are repeatedly integrated Nn times in a time-divisional manner. The multiple integration controller 34 can control the number of times of integration by controlling the integration interval set in the integrating circuit 31.

The multiple integration controller 34 supplies an accumulation rest signal to the accumulating circuit 33 at a timing between the end of the data acquisition interval COA and the beginning of the next data acquisition interval COA.

Figure 15A:
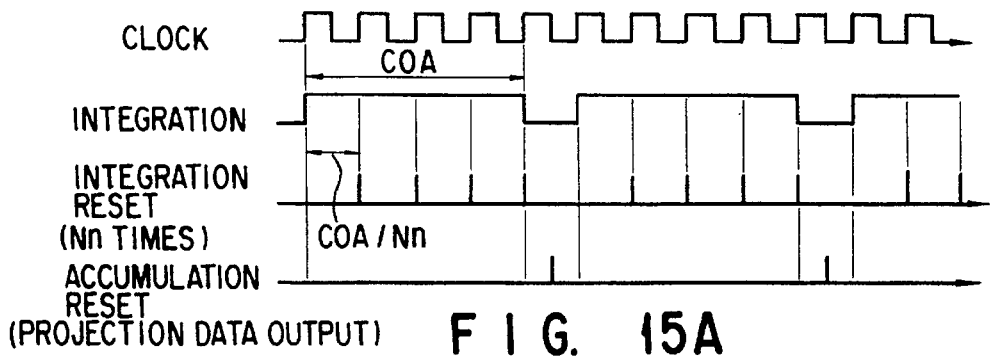
FIGS. 15A and 15B are charts for explaining multiple integration.
Figure 15B:
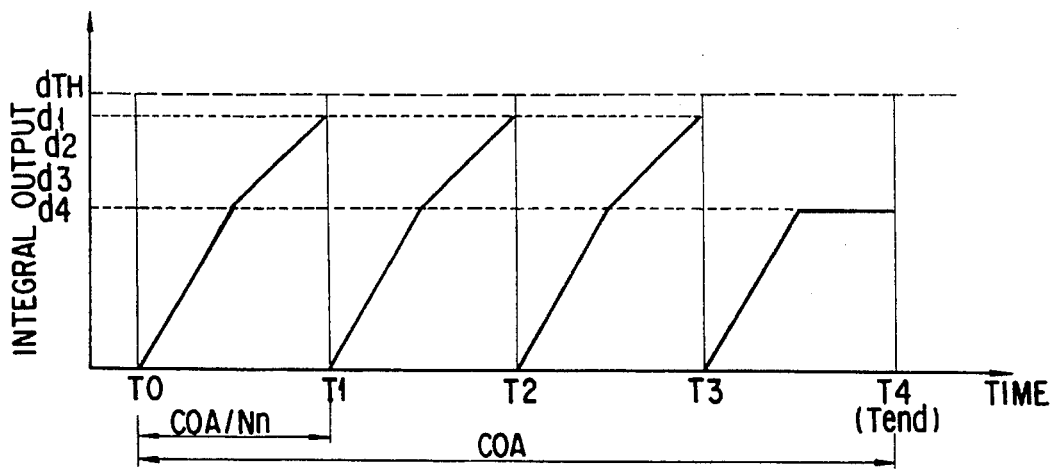

FIG. 14 is a flow chart showing a procedure for multiple integration processing performed in one data acquisition interval COA. FIG. 15A is a timing chart showing the relationship in time between an integration reset signal and an accumulation reset signal in the data acquisition interval COA. FIG. 15B shows the waveforms of time integral signals in a given data acquisition interval. For the sake of descriptive convenience, let n be a parameter representing the number of times of integration, and N be the number of times of integration.

A series of operations from step S42 to step S47 is repeated N times in accordance with the number of times of integration. With this operation, one projection data is created.

Detection signals detected by the X-ray detector 3 are supplied to the integrating circuit 31 via the preamplifier 8 and integrated as a function time (step S42). An integration reset signal is repeatedly supplied from the multiple integration controller 34 to the multiple integrating circuit 30 and the analog/digital converter 32 N times at the predetermined intervals COA/Nn. Every time the integrating circuit 31 receives an integration reset signal, the integrating circuit 31 resets the integral signal to "0", and repeats integration from the zero value (step S43). Every time the analog/digital converter 32 receives an integration reset signal, the analog/digital converter 32 converts the integral signal into a digital signal dn, and sequentially supplies it to the accumulating circuit 33 (step S44). The accumulating circuit 33 accumulates the N digital signals dn (step S45). When such a series of operations is repeated Nn times, the accumulating circuit 33 outputs a cumulative value DN, as projection data, to the reconstruction processing section 15. An accumulation reset signal is then supplied. Upon receiving the accumulation reset signal from the multiple integration controller 34, the accumulating circuit 33 resets the cumulative value to "0", and prepares for the creation of the next projection data (step S49).

By properly increasing/decreasing the number of times of integration, an overflow can be prevented, and the number of times of integration can be minimized regardless of the magnitude of the incident dose.

Figure 16:
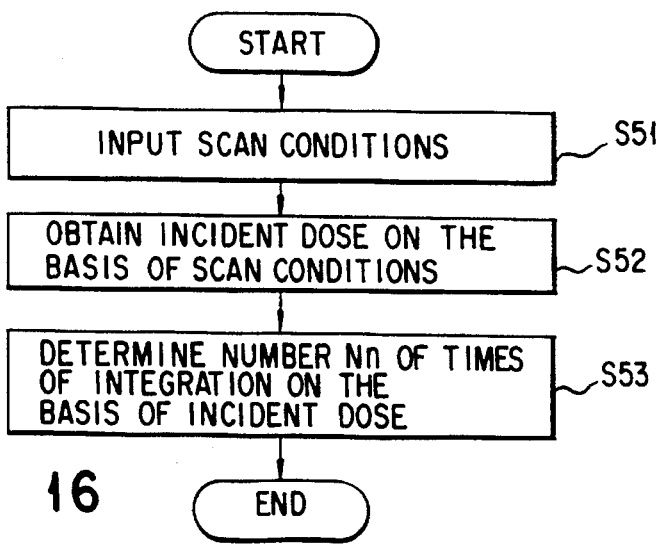
FIG. 16 is a flow chart showing a procedure employed by a multiple integration controller in FIG. 12 to determine the number of times of integration.

FIG. 16 is a flow chart showing a procedure employed by the multiple integration controller 34 to determine the number of times of integration. Scan conditions including a reconstruction area, a tube voltage, a tube current, and a slice thickness are supplied from a scan control section 18 to the multiple integration controller 34 (step S51). The reconstruction area, the tube voltage, the tube current, and the slice thickness required for obtaining an incident dose are extracted from the scan conditions by the multiple integration controller 34, and an incident dose is obtained on the basis of these extracted conditions (step S52). More specifically, an address is created on the basis of the extracted conditions, and incident dose data corresponding to this address is supplied from the memory 35 to the multiple integration controller 34. In addition, an optimal number of times of integration is obtained by the multiple integration controller 34 on the basis of the incident dose (step S53). More specifically, an address is produced on the basis of the incident dose, and the optimal number-of-times-of-integration data corresponding to this address is supplied from the memory 35.

Figure 17A:
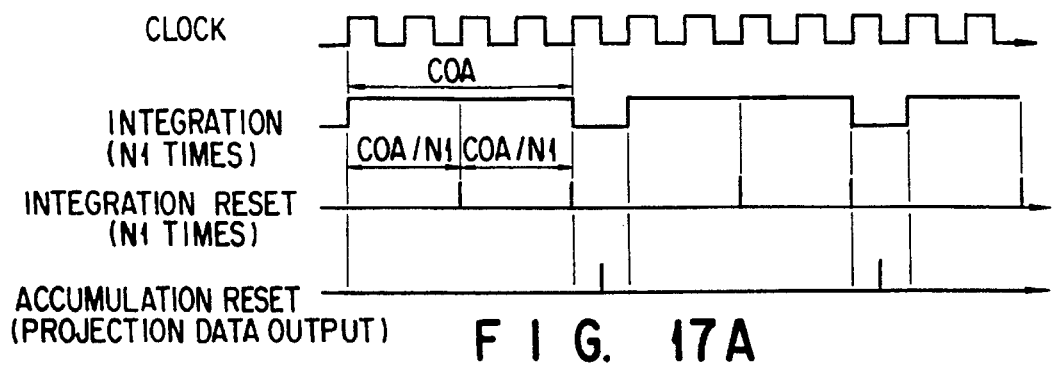
FIGS. 17A and 17B are a timing chart and a graph showing the number of times of integration and an integration interval which are set when the incident dose is relatively small.
Figure 17B:
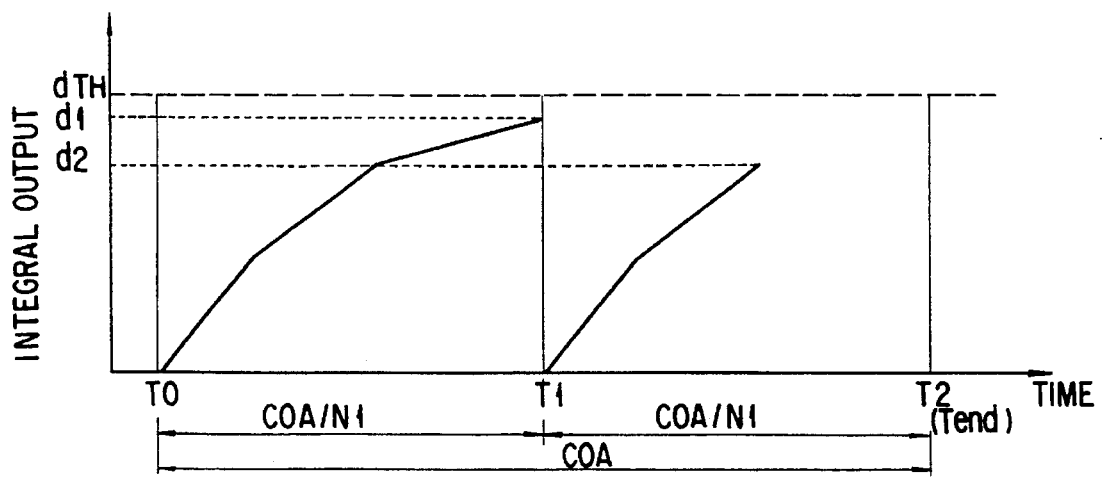
Figure 18A:
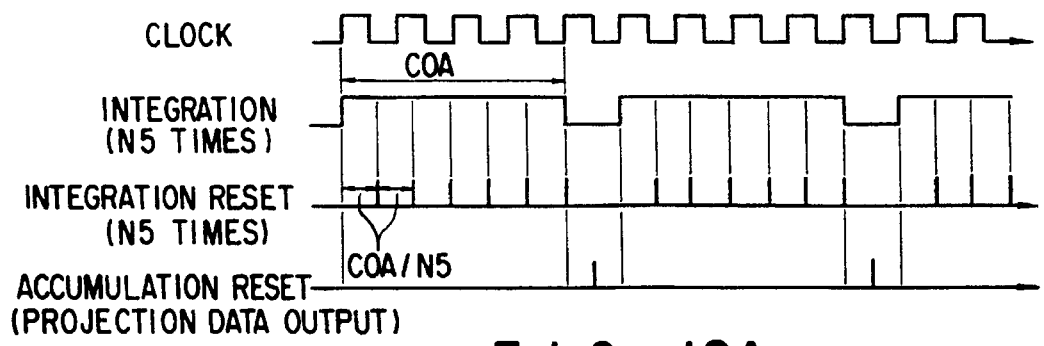

The multiple integration controller 34 obtains a repetition interval (integration interval) of an integration reset signal in accordance with the obtained number N of times of integration according to COA/N, and supplies the integration reset signal to the integrating circuit 31 and the analog/ digital converter 32 at the intervals obtained in this manner. FIGS. 17A and 17B respectively show the number of times of integration and an integration interval which are set when the incident dose is a relatively small dose falling within the range from D1 to D2 in FIG. 13. FIGS. 18A and 18B respectively show the number of times of integration and an integration interval which are set when the incident dose is a relatively large dose falling within the range from D5 to D6 in FIG. 13.

When the incident dose is relatively small, the number of times of integration is decreased. In contrast to this, when the incident dose is relatively large, the number of times of integration is increased. With this operation, the number of times of integration can be minimized while an overflow is prevented.

(Fifth Embodiment)

In the fifth embodiment, similar to the fourth embodiment, the number of times of integration is determined on the basis of scan conditions according to a procedure like the one shown in FIG. 16. This embodiment is characterized in that the current number of times of integration is manually increased/decreased in accordance with an instruction from the operator.

FIG. 19 shows the arrangement of the main part of an X-ray CT according to the fifth embodiment. The same reference numerals in FIG. 19 denote the same parts as in FIG. 12, and a description thereof will be omitted. A console 17 includes a key or switch used by the operator to issue a command (UP/DOWN command) for increasing/decreasing the number of times of integration, in addition to keys or switches for inputting scan conditions and a scan start/end command as in the first embodiment. A multiple integration controller 36 determines the number of times of integration on the basis of scan conditions in the same manner as in the fourth embodiment, and controls a multiple integrating circuit 30 to execute multiple integration according to the determined number of times of integration. Upon receiving an UP/DOWN command for increasing/decreasing the number of times of integration via the console 17, the multiple integration controller 36 increases/decreases the current number of times of integration in accordance with this command and controls the multiple integrating circuit 30 to execute multiple integration according to the increased/decreased number of times of integration.

FIG. 20 is a flow chart showing a procedure employed by the multiple integration controller 36 to increase/decrease the number of times of integration. First of all, let Nn be the current number of times of integration (step S61). A signal (UP signal) for increasing the number of times of integration or a signal (DOWN signal) for decreasing the number of times of integration is supplied to the multiple integration controller 36 via the console 17 (step S62). If it is determined in step S63 that the supplied signal is an UP signal, the current number Nn of times of integration is increased to a number Nn+1 of times (step S64). If the current number of times of integration is N3 in FIG. 13, the number M3 of times is increased by one step to N4. If the supplied signal is a DOWN signal, the current number Mn of times of integration is decreased to Nn−1 (step S65). If, for example, if the current number of times of integration is N3, the number N3 of times is decreased by one step to N2.

As described above, according to this embodiment, the number of times of integration can be manually increased/decreased by the operator.

(Sixth Embodiment)

The sixth embodiment is characterized in that the number of times of integration is optimized for each projection angle on the basis of past projection data which has already been acquired.

FIG. 21 shows the arrangement of the main part of an X-ray CT according to the sixth embodiment. The same reference numerals in FIG. 21 denote the same parts as in FIG. 12, and a description thereof will be omitted. A reconstruction processing section 15 comprises a data memory 39, a reconstruction unit 40, and an image memory 41. Projection data created by a multiple integrating circuit 30 are stored in the data memory 39 at addresses corresponding to scan numbers, channel numbers, and the rotational angles (projection angles) of an X-ray tube 2. The reconstruction unit 40 reconstructs a tomographic image on the basis of projection data having the same scan number and corresponding to, e.g., one rotation. The image memory 41 temporarily stores a tomographic image and outputs it to a display section 16.

Figure 22A:
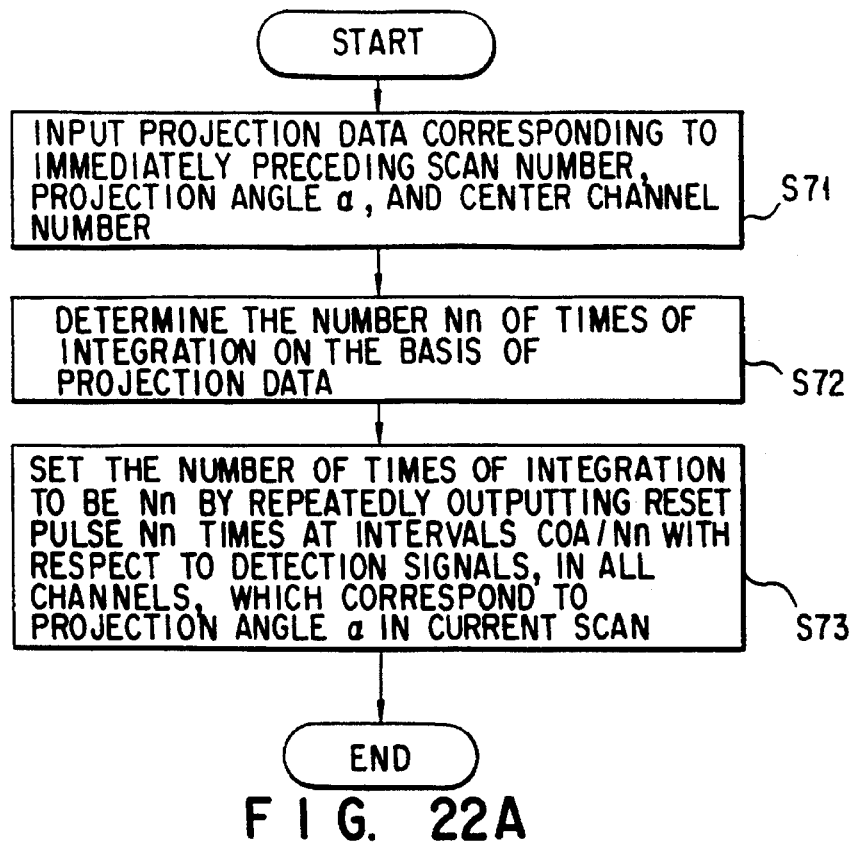
FIGS. 22A and 22B are flow charts, each showing a procedure employed by a multiple integration controller in FIG. 21 to determine and set the number of times of integration.

FIG. 22A is a flow chart showing a procedure employed by a multiple integration controller 37 in a method of determining the number of times of integration. First of all, the multiple integration controller 37 accesses the data memory 39 to input projection data corresponding to a past scan number, preferably an immediately preceding scan number n−1, a rotational angle α, and a center channel number (step S71).

The multiple integration controller 37 accesses a memory 38 in accordance with this projection data to input an optimal number Nn of times of integration which corresponds to the projection data (step S72). Similar to the case shown in FIG. 13, optimal numbers of times of integration are stored in the memory 38 in correspondence with various projection data. A small number of times of integration is caused to correspond to projection data of a relatively low level. With an increase in the level of projection data, the corresponding number of times of integration gradually increases.

The multiple integration controller 37 obtains a repetition interval (integration interval) of an integration reset signal by dividing a predetermined data acquisition interval COA by the number Nn of times of integration. The multiple integration controller 37 realizes the optimal number of times of integration by supplying the integration reset signal to the multiple integrating circuit 30, from the beginning of the data acquisition interval, at the above integration intervals with respect to detection signals, in all the channels, which are detected when the X-ray tube 2 is at the rotational angle α in the current nth scan (step S73).

Such optimization of the number of times of integration is repeated every time the rotational angle (projection angle) of the X-ray tube 2 changes.

According to this embodiment, the number of times of integration can be optimized for each projection angle on the basis of past projection data.

Figure 22B:
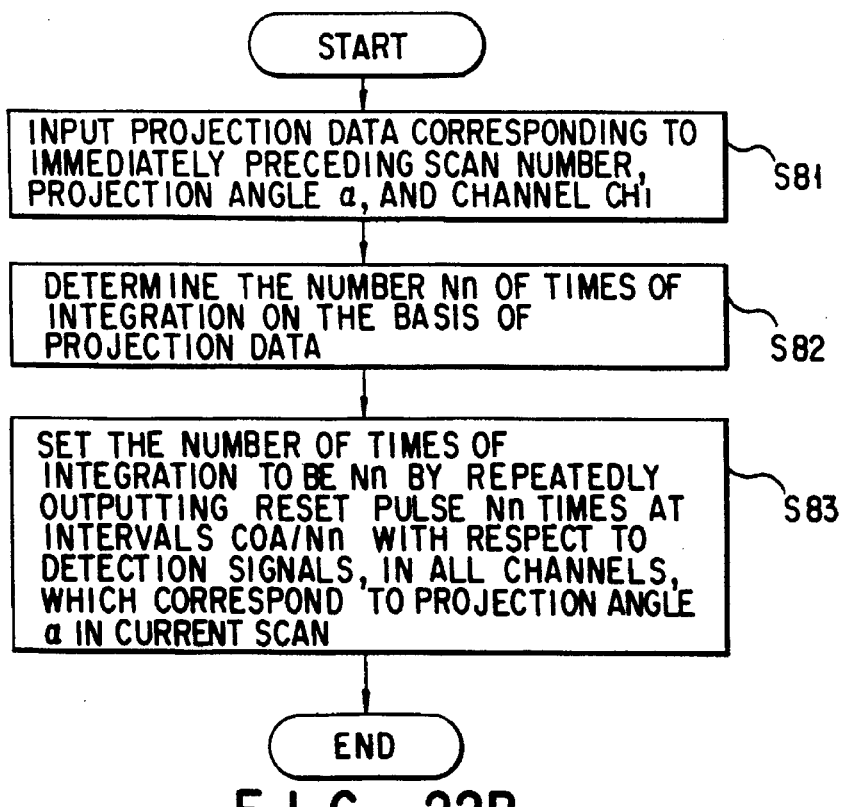

This embodiment can be modified as follows. FIG. 22B is a flow chart showing a procedure in a modified method of determining the number of times of integration. First of all, the multiple integration controller 37 accesses the data memory 39 to input projection data corresponding to a past scan number, preferably an immediately preceding number n−1, a rotational angle α, and the channel number of a channel CHi (step S81).

The multiple integration controller 37 then accesses the memory 38 in accordance with this projection data to input the optimal number Nn of times of integration which corresponds to the projection data (step S82).

The multiple integration controller 37 obtains a repetition interval of an integration reset signal by dividing the data acquisition interval COA by the number Nn of times of integration. The multiple integration controller 37 realizes the optimal number of times of integration by supplying the integration reset signal to the multiple integrating circuit 30, from the beginning of the data acquisition interval COA, at the above repetition intervals with respect to a detection signal, in the channel CHi, which is detected when the X-ray tube 2 is at the rotational angle $\alpha$ in the current nth scan (step S83).

Such optimization of the number of times of integration is performed for each channel.

According to this modification, the number of times of integration can be optimized for each channel and each projection angle on the basis of past projection data.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An X-ray computed tomography apparatus comprising:

X-ray emission means for emitting an X-ray in accordance with a scan condition;

detection means for detecting an X-ray transmitted through an object to be examined;

integrating means for repeatedly integrating a detection signal from said detection means at predetermined intervals;

oversampling means for sampling an integral signal from said integrating means a plurality of number of times in an initial period of the interval and averaging the sampled signals to obtain an initial average value, sampling the integral signal from said integrating means a plurality of number of times in a final period of the interval and averaging the sampled signals to obtain a final average value, and subtracting the initial average value from the final average value to create projection data;

reconstruction means for reconstructing a tomographic image on the basis of a plurality of projection data with different projection angles; and oversampling control means for determining the number of times of sampling on the basis of the scan condition, and controlling said oversampling means to realize the determined number of times of sampling.

2. An apparatus according to claim 1, wherein said oversampling control means obtains a dose of transmitted X-ray on the basis of the scan condition, and determines the number of times of sampling on the basis of the dose.

3. An apparatus according to claim 2, wherein said oversampling means increases the number of times of sampling when the dose is relatively small, and decreases the number of times of sampling when the dose is relatively large.

4. An apparatus according to claim 2, wherein said oversampling means determines a dose on the basis of a tube voltage, a tube current, a slice thickness, and a size of a reconstruction area included in the scan condition.

5. An apparatus according to claim 2, wherein said oversampling control means includes memory means for storing various relationships between scan conditions and doses and various relationships between doses and the numbers of times of sampling.

6. An apparatus according to claim 1, wherein said oversampling means includes memory means for storing various relationships between scan conditions and the numbers of times of sampling.

7. An apparatus according to claim 1, wherein said oversampling means repeats sampling at predetermined intervals, and said oversampling control means controls the intervals at which said oversampling means repeats sampling in accordance with the determined number of times of sampling.

8. An X-ray computed tomography apparatus comprising:

X-ray emission means for emitting an X-ray;

detection means for detecting an X-ray transmitted through an object to be examined;

integrating means for repeatedly integrating a detection signal from said detection means at predetermined intervals;

oversampling means for sampling an integral signal from said integrating means a plurality of number of times in an initial period of the interval and averaging the sampled signals to obtain an initial average value, sampling the integral signal from said integrating means a plurality of number of times in a final period of the interval and averaging the sampled signals to obtain a final average value, and subtracting the initial average value from the final average value to create projection data;

reconstruction means for reconstructing a tomographic image on the basis of a plurality of projection data with different projection angles;

input means for inputting information for increasing/decreasing the number of times of sampling; and oversampling control means for controlling said oversampling means to increase/decrease the number of times of sampling in accordance with the information input from said input means.

9. An apparatus according to claim 8, wherein said oversampling means repeats sampling at predetermined intervals, and said oversampling control means controls the intervals at which said oversampling means repeats sampling.

10. An X-ray computed tomography apparatus comprising:

X-ray emission means for emitting an X-ray;

detection means for detecting an X-ray transmitted through an object to be examined;

integrating means for repeatedly integrating a detection signal from said detection means at predetermined intervals;

oversampling means for sampling an integral signal from said integrating means a plurality of number of times in an initial period of the interval and averaging the sampled signals to obtain an initial average value, sampling the integral signal from said integrating means a plurality of number of times in a final period of the interval and averaging the sampled signals to obtain a final average value, and subtracting the initial average value from the final average value to create projection data;

reconstruction means for reconstructing a tomographic image on the basis of a plurality of projection data with different projection angles; and oversampling control means for determining the number of times of sampling on the basis of a level of past projection data, and controlling said oversampling means to realize the determined number of times of sampling.

11. An apparatus according to claim 10, wherein said oversampling control means increases the number of times of sampling when the level of the projection data is relatively low, and decreases the number of times of sampling when the level of the projection data is relatively high.

12. An apparatus according to claim 10, wherein said oversampling control means includes memory means for storing various relationships between levels of projection data and the numbers of times of sampling.

13. An apparatus according to claim 10, wherein said oversampling means repeats sampling at predetermined intervals, and said oversampling control means controls the intervals at which said oversampling means repeats sampling in accordance with the determined number of times of sampling.

14. An apparatus according to claim 10, wherein said oversampling control means determines the number of times of sampling on the basis of a plurality of projection data with different projection angles, and controls the number of times of sampling for each projection angle.

15. An X-ray computed tomography apparatus comprising:

X-ray emission means for emitting an X-ray in accordance with a scan condition;

detection means for detecting an X-ray transmitted through an object to be examined;

multiple integrating means for repeatedly integrating a detection signal from said detection means at predetermined intervals, and accumulating repeatedly obtained integral values, thereby creating projection data;

reconstruction means for reconstructing a tomographic image on the basis of a plurality of projection data with different projection angles; and multiple integration control means for determining the number of times of integration on the basis of the scan condition, and controlling said multiple integrating means to realize the determined number of times of integration.

16. An apparatus according to claim 15, wherein said multiple integration control means obtains a dose of transmitted X-ray on the basis of the scan condition, and determines the number of times of integration on the basis of the dose.

17. An apparatus according to claim 16, wherein said multiple integration control means decreases the number of times of integration when the dose is relatively small, and increases the number of times of integration when the dose is relatively large.

18. An apparatus according to claim 16, wherein said multiple integration control means determines a dose on the basis of a tube voltage, a tube current, a slice thickness, and a size of a reconstruction area included in the scan condition.

19. An apparatus according to claim 16, wherein said multiple integration control means includes memory means for storing various relationships between scan conditions and doses and various relationships between doses and the numbers of times of integration.

20. An apparatus according to claim 15, wherein said multiple integration control means includes memory means for storing various relationships between scan conditions and the numbers of times of integration.

21. An apparatus according to claim 16, wherein said multiple integration control means controls a repetition interval of integration in accordance with the determined number of times of integration.

22. An X-ray computed tomography apparatus comprising:

X-ray emission means for emitting an X-ray;

detection means for detecting an X-ray transmitted through an object to be examined;

multiple integrating means for repeatedly integrating a detection signal from said detection means at predetermined intervals, and accumulating repeatedly obtained integral values, thereby creating projection data;

reconstruction means for reconstructing a tomographic image on the basis of a plurality of projection data with different projection angles;

input means for inputting information for increasing/decreasing the number of times of integration; and multiple integration control means for controlling said multiple integration means to increase/decrease the number of times of integration in accordance with the information input from said input means.

23. An apparatus according to claim 22, wherein said multiple integration control means controls a repetition interval of integration in accordance with the determined number of times of integration.

24. An X-ray computed tomography apparatus comprising:

X-ray emission means for emitting an X-ray;

detection means for detecting an X-ray transmitted through an object to be examined;

multiple integrating means for repeatedly integrating a detection signal from said detection means at predetermined intervals, and accumulating repeatedly obtained integral values, thereby creating projection data;

reconstruction means for reconstructing a tomographic image on the basis of a plurality of projection data with different projection angles; and multiple integration control means for determining the number of times of integration on the basis of past projection data, and controlling said multiple integrating means to realize the determined number of times of integration.

25. An apparatus according to claim 24, wherein said multiple integration control means decreases the number of times of integration when a level of the projection data is relatively low, and increases the number of times of integration when the level of the projection data is relatively high.

26. An apparatus according to claim 24, wherein said multiple integration control means includes memory means for storing various relationships between levels of projection data and the numbers of times of integration.

27. An apparatus according to claim 24, wherein said multiple integration control means controls a repetition interval of integration in accordance with the determined number of times of integration.

28. An apparatus according to claim 24, wherein said multiple integration control means determines the number of times of integration for each projection angle on the basis of a plurality of projection data with different projection angles, and controls the number of times of integration for each projection angle.

* * * * *